(12) United States Patent  
Kendall

(10) Patent No.: US 8,416,418 B2
(45) Date of Patent: Apr. 9, 2013

(54) METHOD AND APPARATUS FOR GOLD DETECTION

(75) Inventor: James D. Kendall, Ajax (CA)

(73) Assignee: Kendall Technology Inc., Ajax, Ontario (CA)

( * ) Notice: Subject to any disclaimer, the term of this patent is extended or adjusted under 35 U.S.C. 154(b) by 12 days.

(21) Appl. No.: 13/182,871

(22) Filed: Jul. 14, 2011

(65) Prior Publication Data

US 2013/0016356 A1 Jan. 17, 2013

(51) Int. Cl.
*G01N 21/55* (2006.01)
(52) U.S. Cl. .......................... 356/445; 356/448
(58) Field of Classification Search .............. 356/445, 356/448, 32, 35, 73.1, 73, 402, 303, 306, 356/309, 317, 319, 320, 326, 332, 407, 408, 356/411, 412, 414, 416, 419–420, 425; 250/326, 250/216, 339.09, 339.12, 336.1; 209/588, 209/576, 577; 436/164, 94, 171; 422/82.05, 422/82.09
See application file for complete search history.

(56) References Cited

U.S. PATENT DOCUMENTS

| | | | |
|---|---|---|---|
| 3,316,545 A | 4/1967 | Reed | |
| 3,395,987 A | 8/1968 | Nakagawa et al. | |
| 3,397,040 A | 8/1968 | Lakin et al. | |
| 3,702,735 A | 11/1971 | Potter | |
| 3,910,701 A | 10/1975 | Henderson et al. | |
| 4,324,555 A | 4/1982 | Borst | |
| 4,345,840 A | 8/1982 | Goetz et al. | |
| 5,946,102 A | 8/1999 | Holcomb | |
| 6,624,888 B2 | 9/2003 | Panigrahi et al. | |
| 6,686,202 B2 | 2/2004 | Furlong et al. | |
| 6,875,254 B2 | 4/2005 | Furlong et al. | |
| 7,236,243 B2 * | 6/2007 | Beecroft et al. | 356/328 |
| 7,368,292 B2 | 5/2008 | Hummel et al. | |
| 7,924,414 B2 | 4/2011 | Mound | |
| 2002/0011567 A1 | 1/2002 | Ozanich | |
| 2005/0229698 A1 | 10/2005 | Beecroft et al. | |
| 2010/0041161 A1 | 2/2010 | Ferrao De Paiva Martins et al. | |
| 2010/0277740 A1 | 11/2010 | Hulteen et al. | |
| 2010/0305418 A1 * | 12/2010 | Deliwala | 600/324 |
| 2011/0176135 A1 * | 7/2011 | Yu et al. | 356/433 |

OTHER PUBLICATIONS

International Search Report dated Oct. 25, 2012, International Application No. PCT/CA2012/000660.
Canadian Office Action dated Mar. 2, 2012, Canadian Patent Application No. 2,746,605.

\* cited by examiner

*Primary Examiner* — Tri T Ton
(74) *Attorney, Agent, or Firm* — Bereskin & Parr LLP/S.E.N.C.R.L., s.r.l.

(57) ABSTRACT

A gold detection apparatus capable of detecting gold in field mineral samples such as rock or soil with little or no preparation. Light in red and violet wavelengths is directed at a surface of a mineral sample and the reflected light intensity is measured by an array of sensors or pixels. Based on the characteristic reflectance properties of gold, the reflected light intensity in each wavelength is used to determine the presence of gold particles.

20 Claims, 15 Drawing Sheets

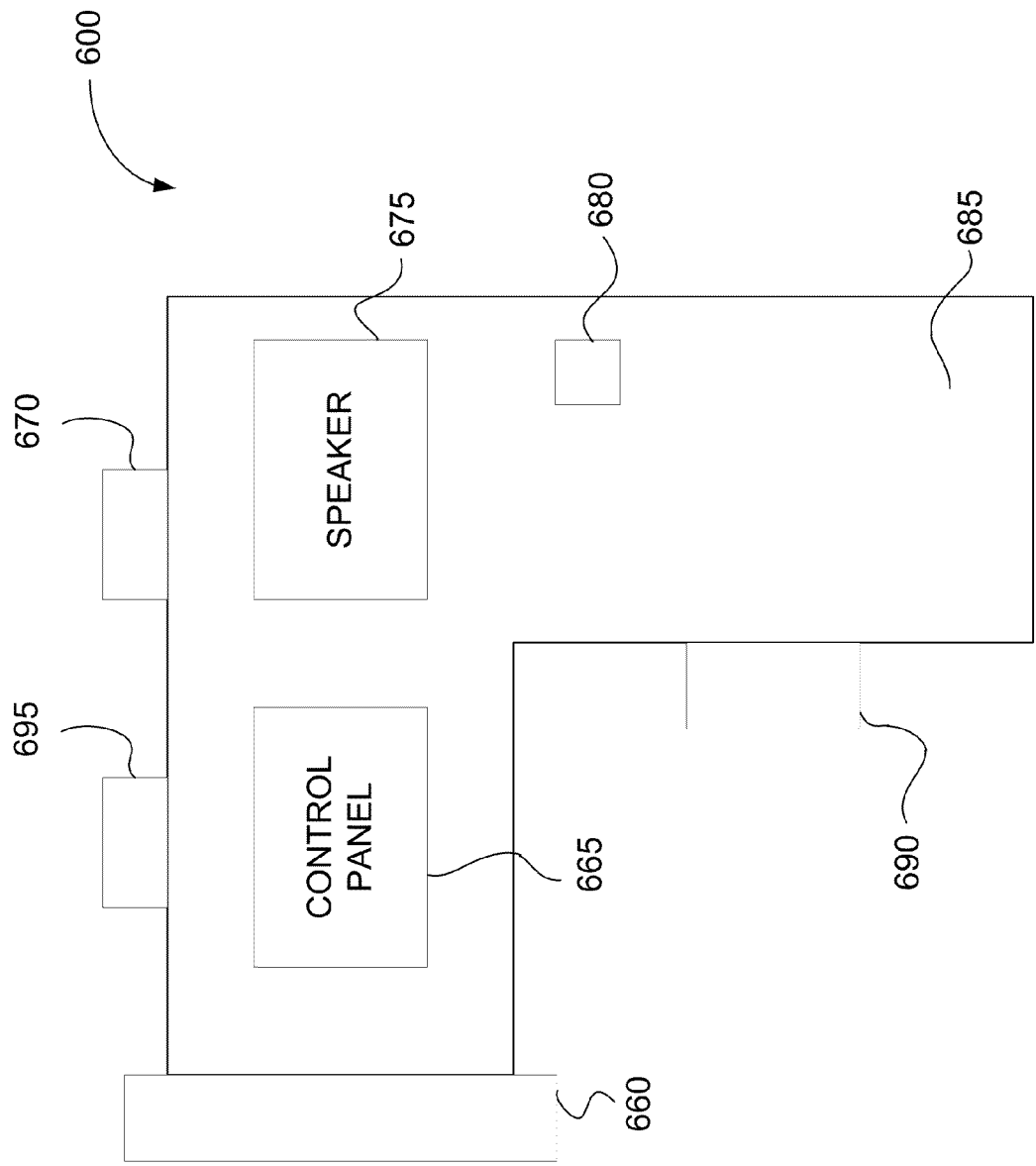

METHOD AND APPARATUS FOR GOLD DETECTION

FIELD

The embodiments described herein relate to a method and apparatus for the detection of metals and, in particular, to the detection of gold and alloys of gold and silver, commonly called electrum, in mineral and material samples taken in the field.

INTRODUCTION

Gold can be found naturally in many, if not most, countries of the world. In each case, the concentration and occurrence of gold may vary. In particular, gold may occur in one or more of the following forms: placer gold (dust to nugget size); visible gold; particulate and micron-sized gold (not visible to the eye at mineral grain boundaries); micron-sized gold (particles greater than 0.2 μm across) within host minerals; colloidal gold (particles less than 0.2 μm across); in solid solution (e.g., where gold is substituted for another metal atom in the structure of a mineral); and in gold minerals (e.g., where gold forms chemical bonds with other atoms).

The detection of gold in particulate, micron and submicron sizes is of particular interest in field exploration and mining applications. The majority of gold deposits typically have gold grains at micron or larger sizes. For example, FIGS. 1A and 1B illustrate optical microscope images of samples taken from several structurally hosted lode gold systems along the Ashanti gold belt in Ghana.

Referring now to FIG. 1A, there are shown four optical microscope images of micron-sized gold particles associated with sulphide and arsenide minerals from the Ashanti gold belt in Ghana, as described by Mumin, A. H. "Early Proterozoic Gold Mineralization of the Bogosu and Prestea Districts of the Ashanti Gold Belt, Ghana, West Africa." Ph.D. thesis, University of Western Ontario, 1994. Micron-sized gold particles can be observed hosted in, or intergrown with: chalcopyrite, arsenopyrite and sphalerite in image 110; sphalerite and albite in image 120; pyrite, sphalerite, chalcopyrite and quartz in image 130; and pyrite and arsenopyrite in image 140.

Referring now to FIG. 1B, there are shown another four optical microscope images of micron-sized gold particles associated with sulphide and arsenide minerals from the Ashanti gold belt in Ghana. Micron-sized gold particles can be observed hosted in, or intergrown with: arsenian pyrite in image 150; pyrite, arsenopyrite and tetrahedrite in image 160; albite, ankerite and siderite in image 170; and sphalerite, siderite, rutile and quartz in image 180.

Typical gold grades encountered during field exploration are in the range of 10-1000 parts per billion (ppb). Mining operations typically encounter gold in concentrations of 0.5 to 10 grams per tonne (g/tonne), which may also be expressed as parts per million (ppm).

One technique that is used in field exploration and mining involves the use of X-ray fluorescence (XRF) to detect the presence of gold, or elements that may indicate the presence of gold such as arsenic. However, portable XRF analyzers are not currently sensitive enough to detect gold at typical economic grades of between 0.5-10 g/tonne, or at lower anomalous values important for exploration.

SUMMARY

In a first broad aspect, there is provided a method for detecting gold in a material sample. The method may comprise: illuminating the material sample with light in a first preselected wavelength range and with light in a second preselected wavelength range; detecting the light in the first preselected wavelength range reflected by the material sample and the light in the second preselected wavelength range reflected by the material sample; and comparing, using a processor, a relative intensity of the reflected light in the first preselected wavelength range to the reflected light in the second preselected wavelength range.

In some embodiments, the material sample can be substantially simultaneously illuminated in the first preselected wavelength range and in the second preselected wavelength range. In some other embodiments, the material sample can be sequentially illuminated in the first preselected wavelength range and in the second preselected wavelength range.

In some embodiments, b) can be carried out by an image sensor comprising a two-dimensional matrix of sensor elements, and c) may comprise comparing the relative intensity for each sensor element in the two-dimensional matrix of sensor elements to compute a weighted intensity value for each sensor element.

In some embodiments, the method may further comprise comparing the relative intensity of the reflected light in the first preselected wavelength range detected at each sensor element in the two-dimensional matrix of sensor elements to an average relative intensity of the reflected light in the first preselected wavelength range detected the two-dimensional matrix of sensor elements.

In some embodiments, the first preselected wavelength range can be in the BV (blue-violet) spectrum, and the second preselected wavelength range can be in the ROY (red-orange-yellow) spectrum.

In some embodiments, the reflected light in the first preselected wavelength range may comprise substantially monochromatic light with a wavelength less than 500 nm, and the reflected light in the second preselected wavelength range may comprise substantially monochromatic light with a wavelength greater than 500 nm.

In some embodiments, the reflected light can be filtered to isolate the first preselected wavelength range, and the reflected light can be separately filtered to isolate the second preselected wavelength range.

In some embodiments, the method may further comprise detecting ambient light reflected by the material sample, wherein the detected ambient light reflected by the material sample can be used to reduce noise when computing the relative intensity in c).

In a second broad aspect, there is provided an apparatus for detecting gold in a material sample. The apparatus may comprise: at least one light source for illuminating the material sample with light in a first preselected wavelength range and with light in a second preselected wavelength range; an image sensor for detecting the light in the first preselected wavelength range reflected by the material sample and the light in the second preselected wavelength range reflected by the material sample; and a processor, for comparing a relative intensity of the reflected light in the first preselected wavelength range to the reflected light in the second preselected wavelength range.

In some embodiments, the image sensor may comprise a two-dimensional matrix of sensor elements, and the processor may compare the relative intensity for each sensor element in the two-dimensional matrix of sensor elements to compute a weighted intensity value for each sensor element.

In some embodiments, the processor may also be configured to compare the relative intensity of the reflected light in the first preselected wavelength range detected at each sensor element in the two-dimensional matrix of sensor elements to an average relative intensity of the reflected light in the first preselected wavelength range detected by the two-dimensional matrix of sensor elements.

In some embodiments, each sensor element may comprise a first sub-element sensitive to the first preselected wavelength range and a second sub-element sensitive to the second preselected wavelength range.

In some embodiments, the first preselected wavelength range can be in the BV spectrum, and the second preselected wavelength range can be in the ROY spectrum.

In some embodiments, the reflected light in the first preselected wavelength range may comprise substantially monochromatic light with a wavelength less than 500 nm, and the reflected light in the second preselected wavelength range may comprise substantially monochromatic light with a wavelength greater than 500 nm.

In some embodiments, the image sensor can be configured to detect ambient light reflected by the material sample, and the processor can be configured to use the detected ambient light reflected by the material sample to reduce noise when computing the relative intensity.

In some embodiments, the apparatus may further comprise: a first lens element, the first lens element for focusing light reflected by the material sample onto the image sensor. In some embodiments, the apparatus may further comprise a second lens element, the second lens element for diffusing light from the at least one light source onto the material sample. The second lens element may be an end of an optical fiber In some embodiments, the at least one light source may comprise a first laser source for transmitting light in the first preselected wavelength range and a second laser source for transmitting light in the second preselected wavelength range. In some other embodiments, the at least one light source can be a broad spectrum light source, and the apparatus may further comprise a first filter element to filter the reflected light to isolate the first preselected wavelength range, and a second filter element to filter the reflected light to isolate the second preselected wavelength range.

In some embodiments, the image sensor can be selected from the group consisting of a CCD image sensor and a CMOS image sensor.

In some embodiments, the apparatus may further comprise a portable enclosure, the portable enclosure housing the at least one light source, the image sensor and the processor.

In a third broad aspect, there is provided a non-transitory computer-readable storage medium with an executable program stored thereon. The executable program may be configured to instruct a processor to perform a method for detecting gold in a material sample, the method comprising: illuminating the material sample with light in a first preselected wavelength range and with light in a second preselected wavelength range; detecting the light in the first preselected wavelength range reflected by the material sample and the light in the second preselected wavelength range reflected by the material sample; and comparing a relative intensity of the reflected light in the first preselected wavelength range to the reflected light in the second preselected wavelength range.

DRAWINGS

For a better understanding of the embodiments described herein and to show more clearly how they may be carried into effect, reference will now be made, by way of example only, to the accompanying drawings which show at least one exemplary embodiment, and in which:

FIG. 1A provides four optical microscope images of micron-sized gold particles; and FIG. 1B provides another four optical microscope images of micron-sized gold particles.

FIG. 6 is a diagram of an exemplary portable enclosure for the apparatus according to some embodiments.

Figure 1A:
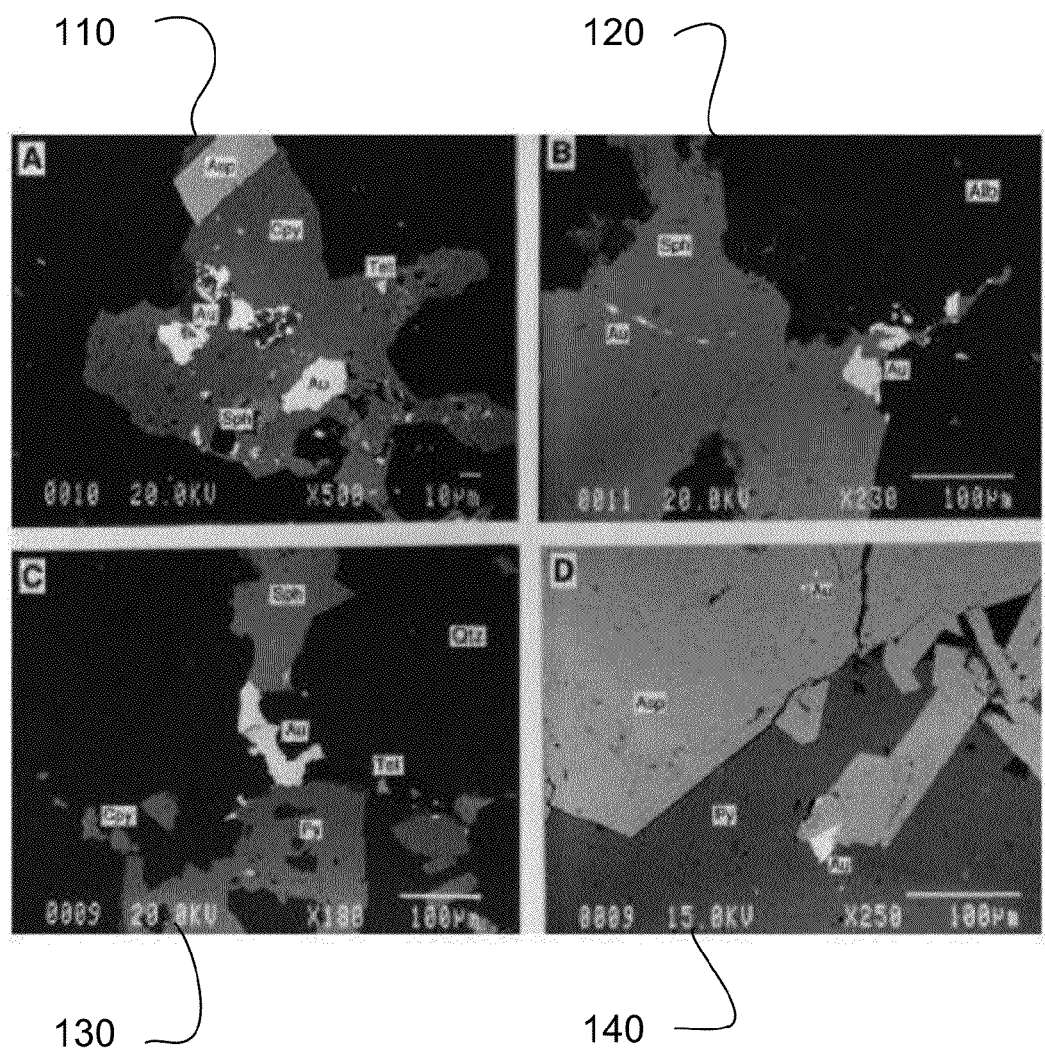
FIG. 1C is an exemplary plot of optical reflectance as a function of wavelength for three metals.
Figure 1B:
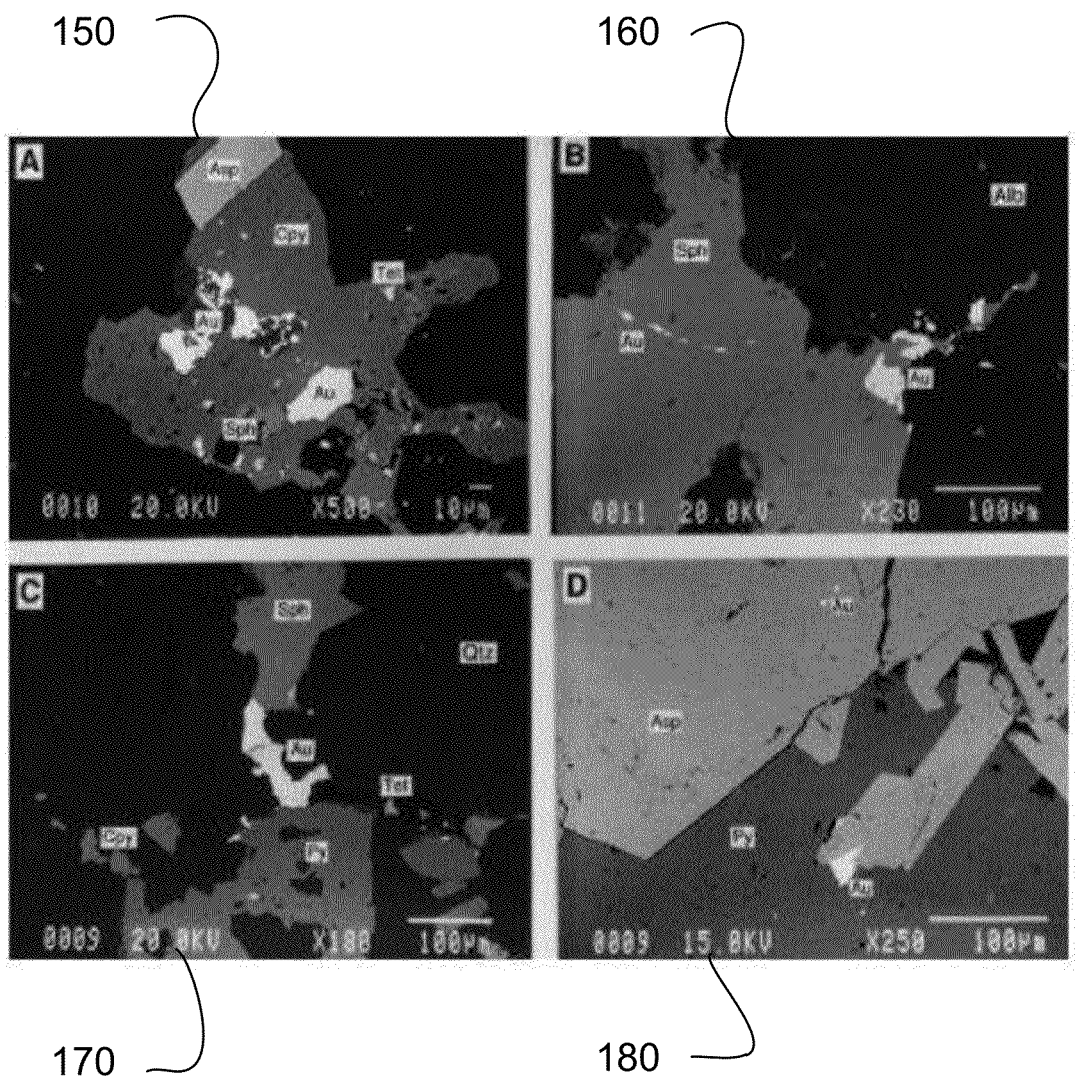

The skilled person in the art will understand that the drawings, described below, are for illustration purposes only. It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

A basic physical property of gold is its high optical reflectance in the red, orange and yellow part of the visible spectrum (i.e., where the wavelength of light is greater than 500 nm) and its relatively lower optical reflectance in the blue and violet part of the visible spectrum (i.e., where the wavelength of light is lower than 500 nm).

The optical reflectance of gold can be lower by a factor of about three in blue and violet (BV) light, as compared to its reflectance in red, orange and yellow (ROY) light. This relatively unique optical property is what gives gold its characteristic brilliant colour, and it is a consequence of relativistic effects in the outer electron orbitals of the gold atom. Such relativistic effects account for the rapid change in the reflectance of gold and silver as a function of the wavelength of incident light. These relativistic effects are described in further detail by Pyykko, P. and Desclaux, J. P., "Relativity and the Periodic System of Elements", Journal of the American Chemical Society, Accounts of Chemical Research, 1979, 12, 276; Pyykko, P., "Relativistic Effects in Structural Chemistry", Chemical Review, 1988, 88, 563-594; and Schwerdtfeger, P., "Relativistic Effects in Properties of Gold", Heteroatom Chemistry, 2002, Vol. 13, No. 6, 578-584, the contents of which are incorporated herein by reference.

Figure 1C:
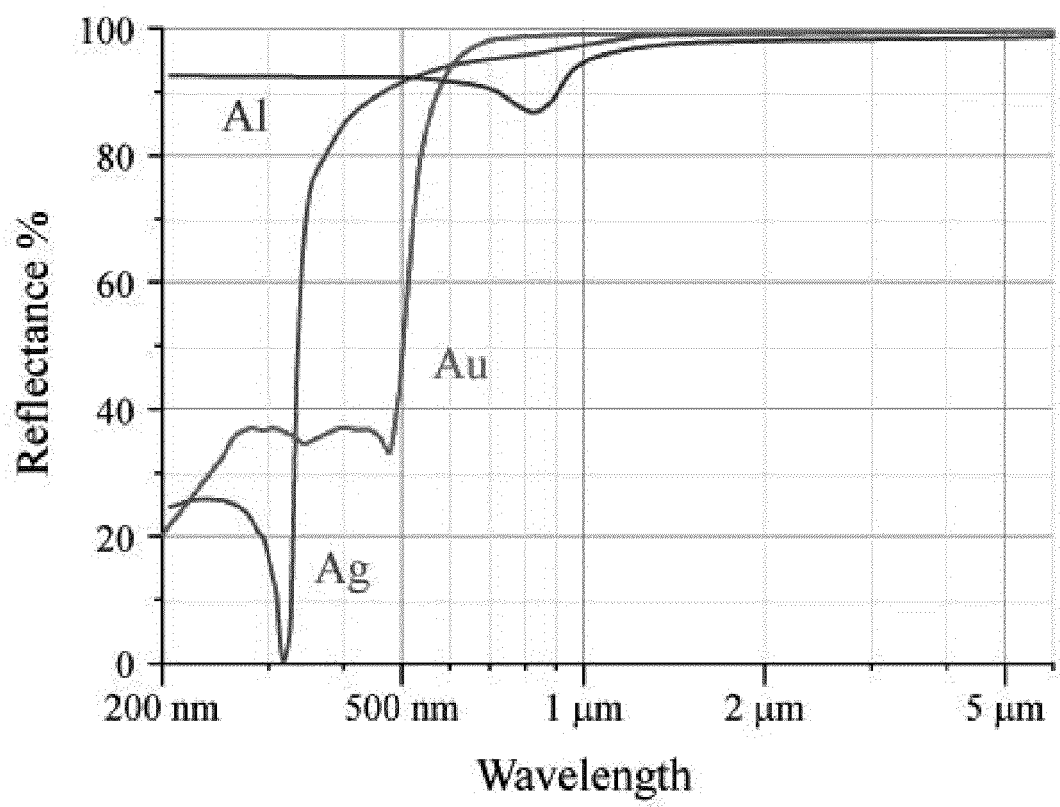
Figure 2A:
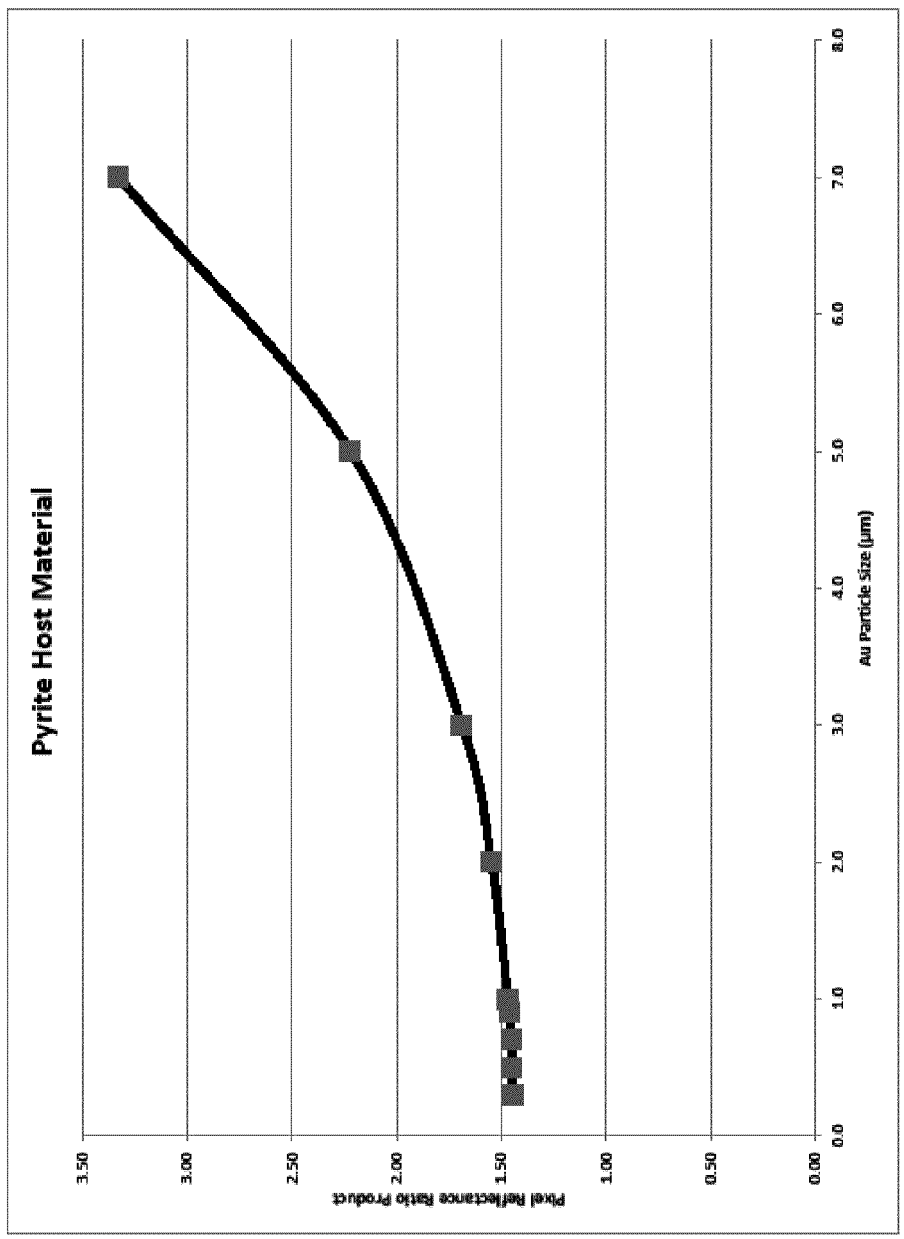
FIG. 2A is an exemplary plot of Reflectance Ratio Product against gold particle diameter for gold hosted in pyrite.
Figure 2B:
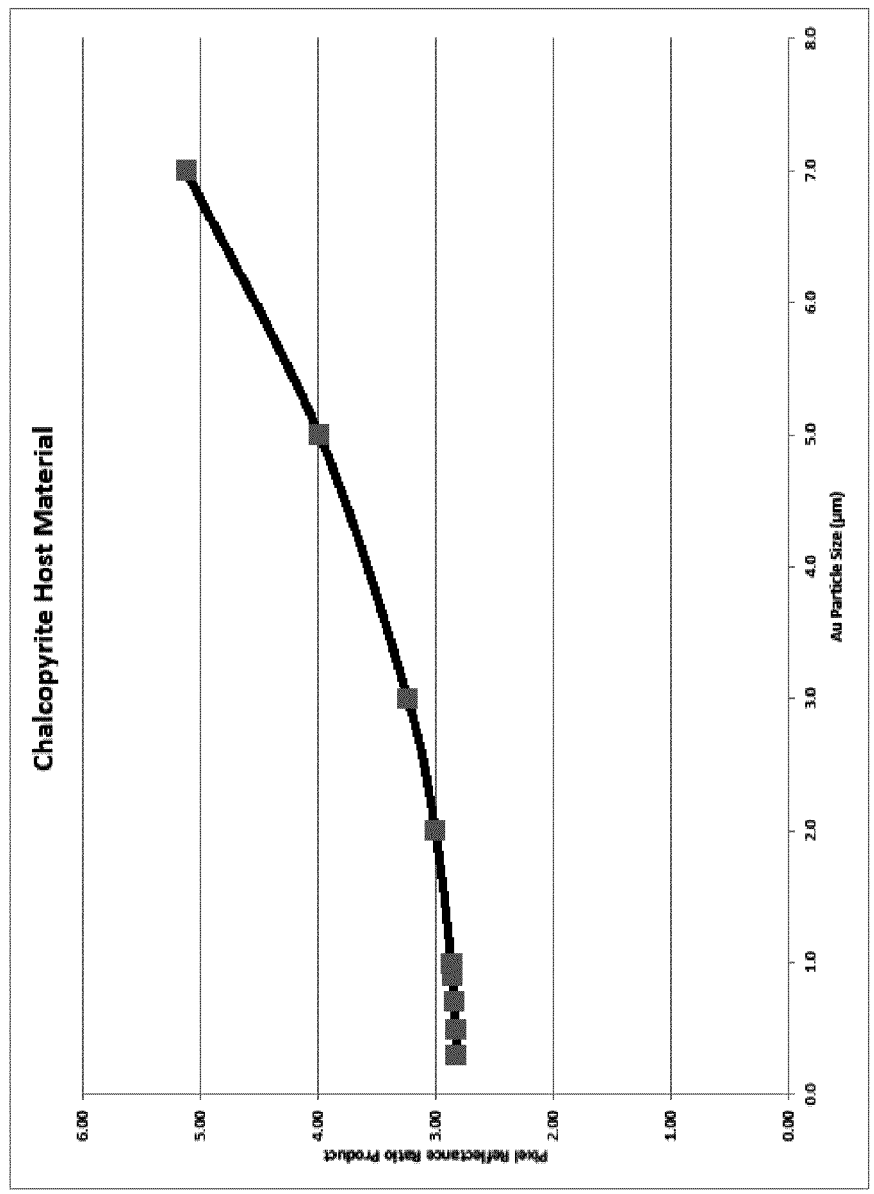
FIG. 2B is an exemplary plot of Reflectance Ratio Product against gold particle diameter for gold hosted in chalcopyrite.
Figure 2C:
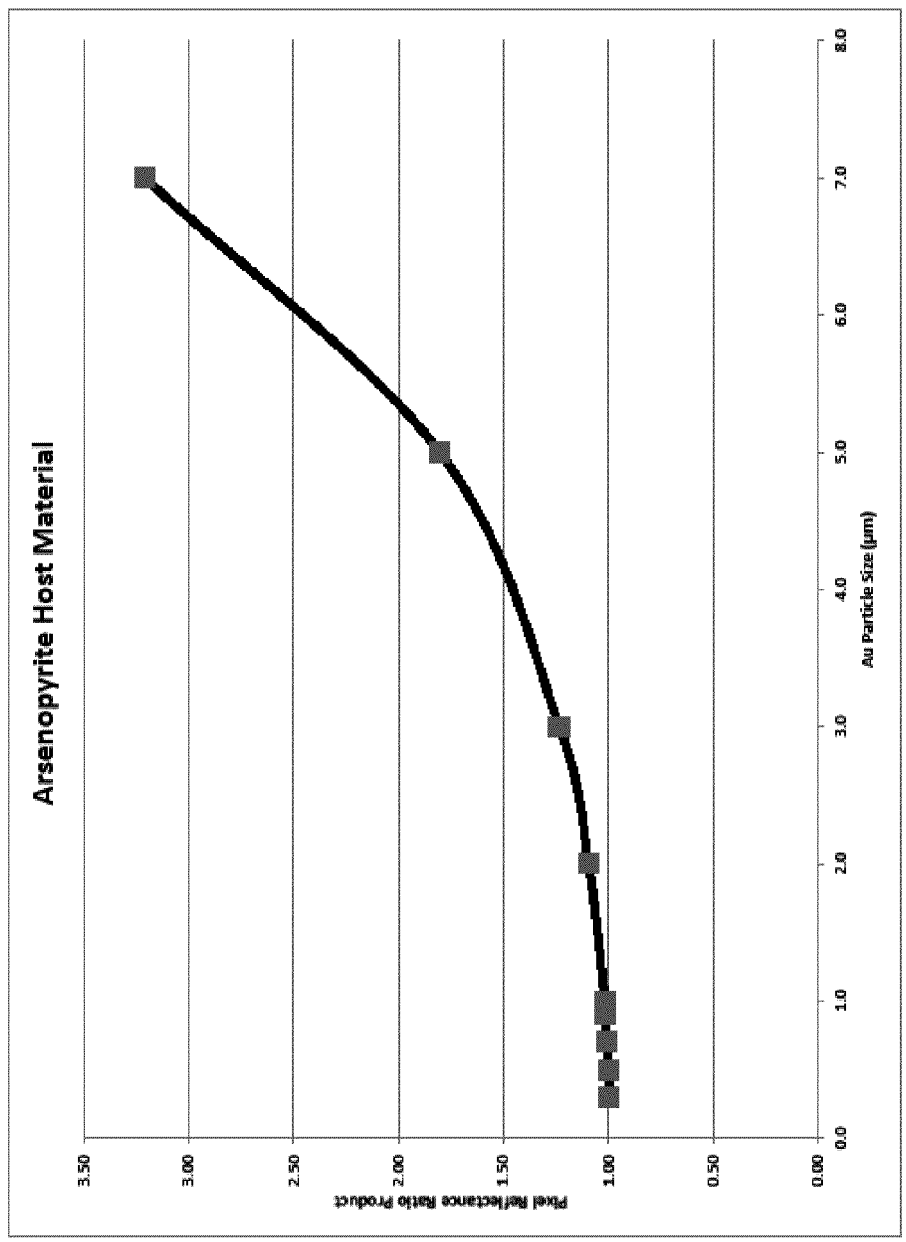
FIG. 2C is an exemplary plot of Reflectance Ratio Product against gold particle diameter for gold hosted in arsenopyrite.
Figure 2D:
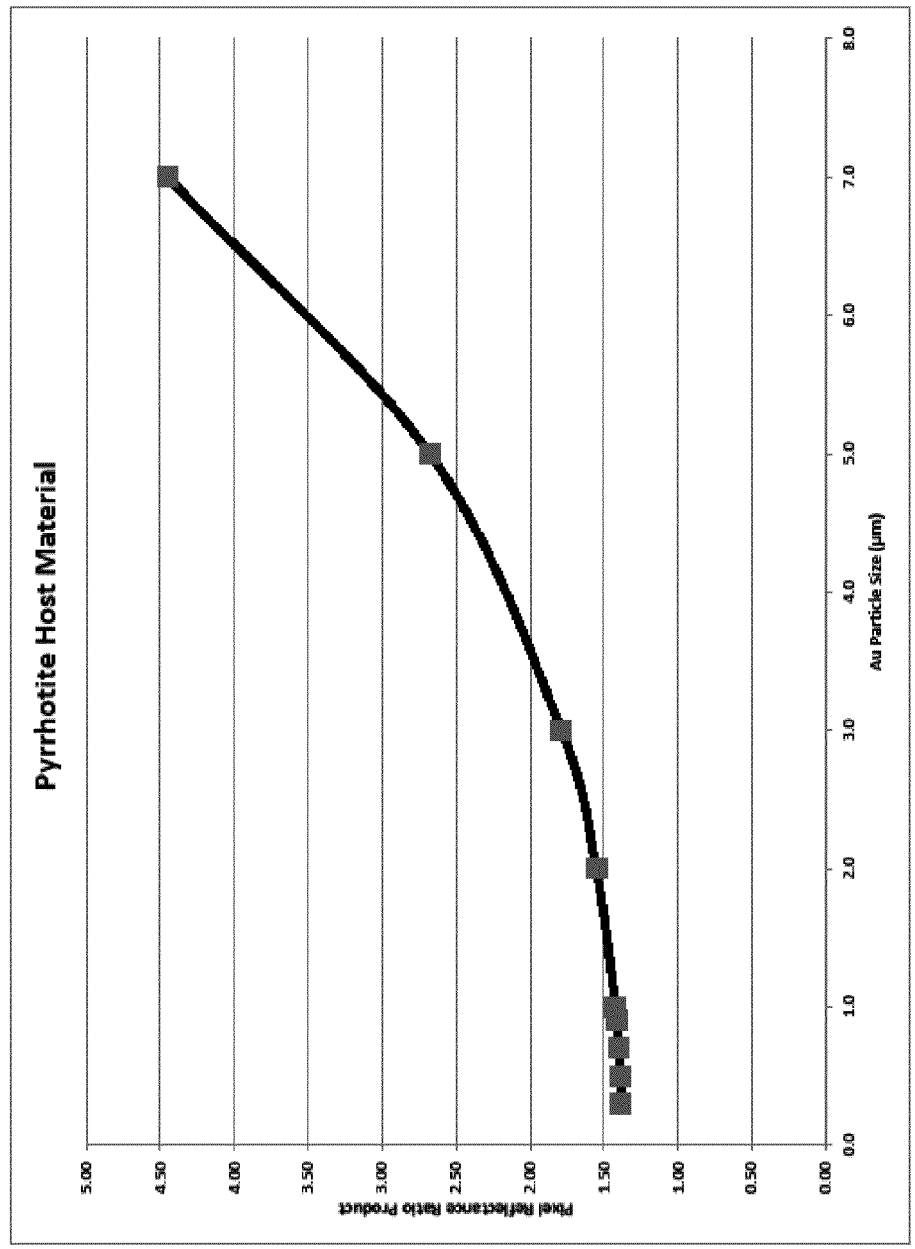
FIG. 2D is an exemplary plot of Reflectance Ratio Product against gold particle diameter for gold hosted in pyrrhotite.
Figure 2E:
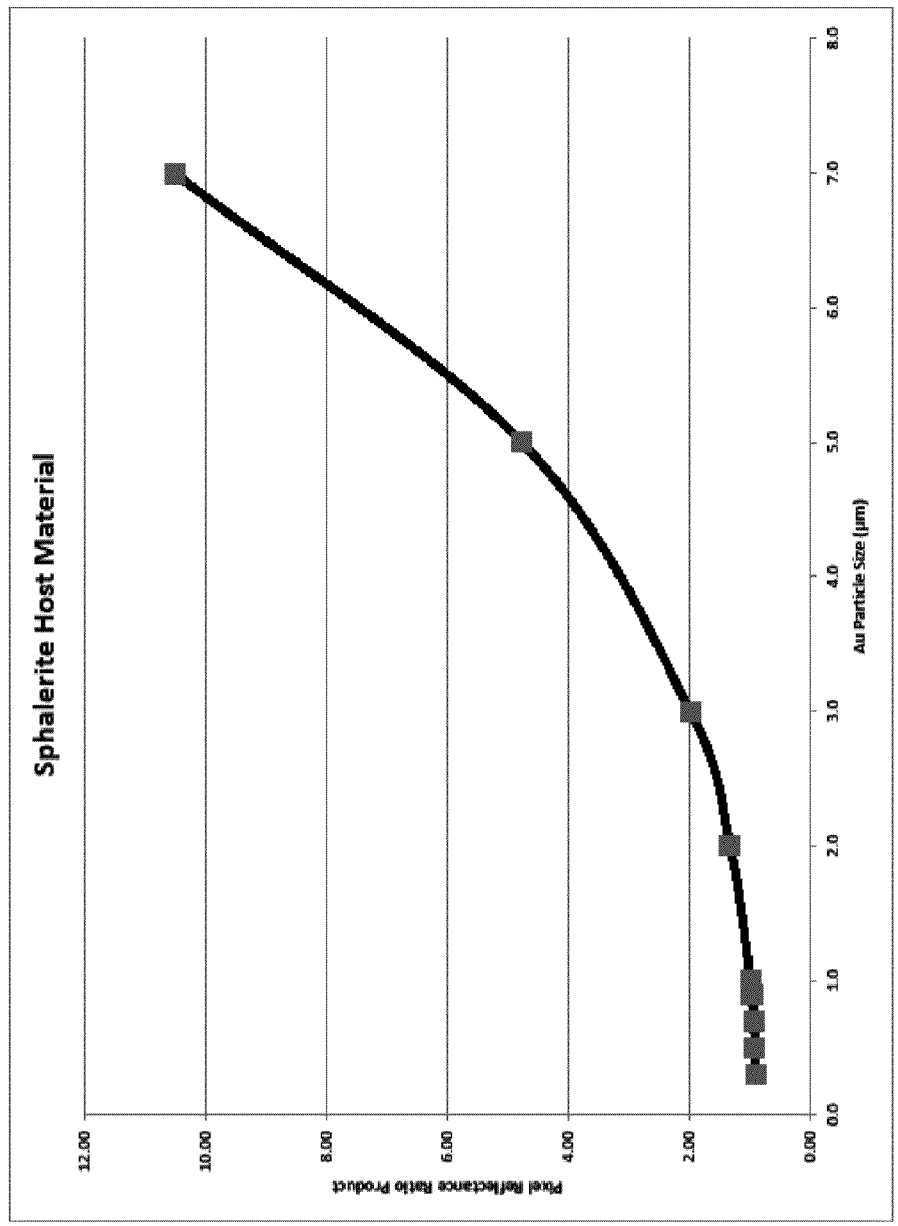
FIG. 2E is an exemplary plot of Reflectance Ratio Product against gold particle diameter for gold hosted in sphalerite.
Figure 2F:
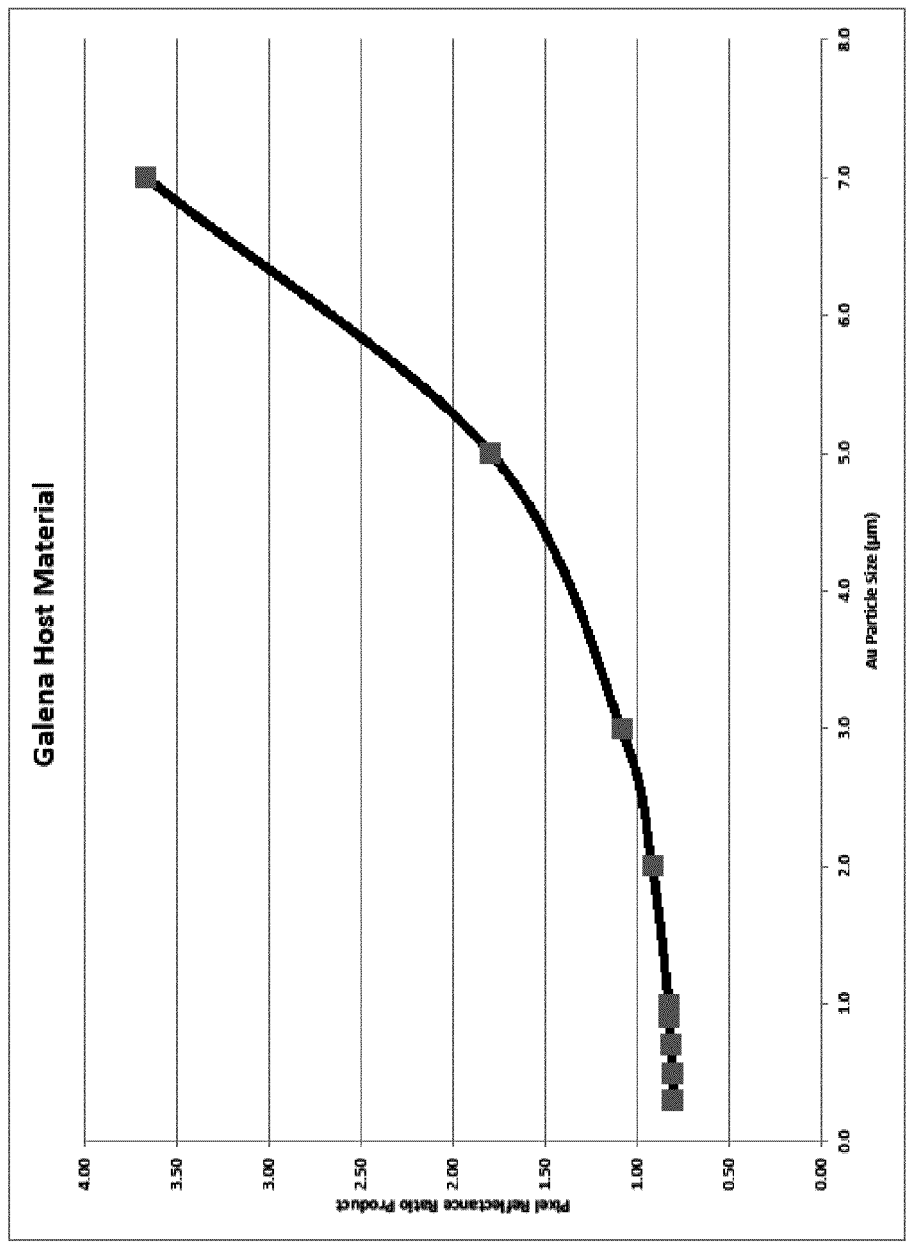
FIG. 2F is an exemplary plot of Reflectance Ratio Product against gold particle diameter for gold hosted in galena.
Figure 2G:
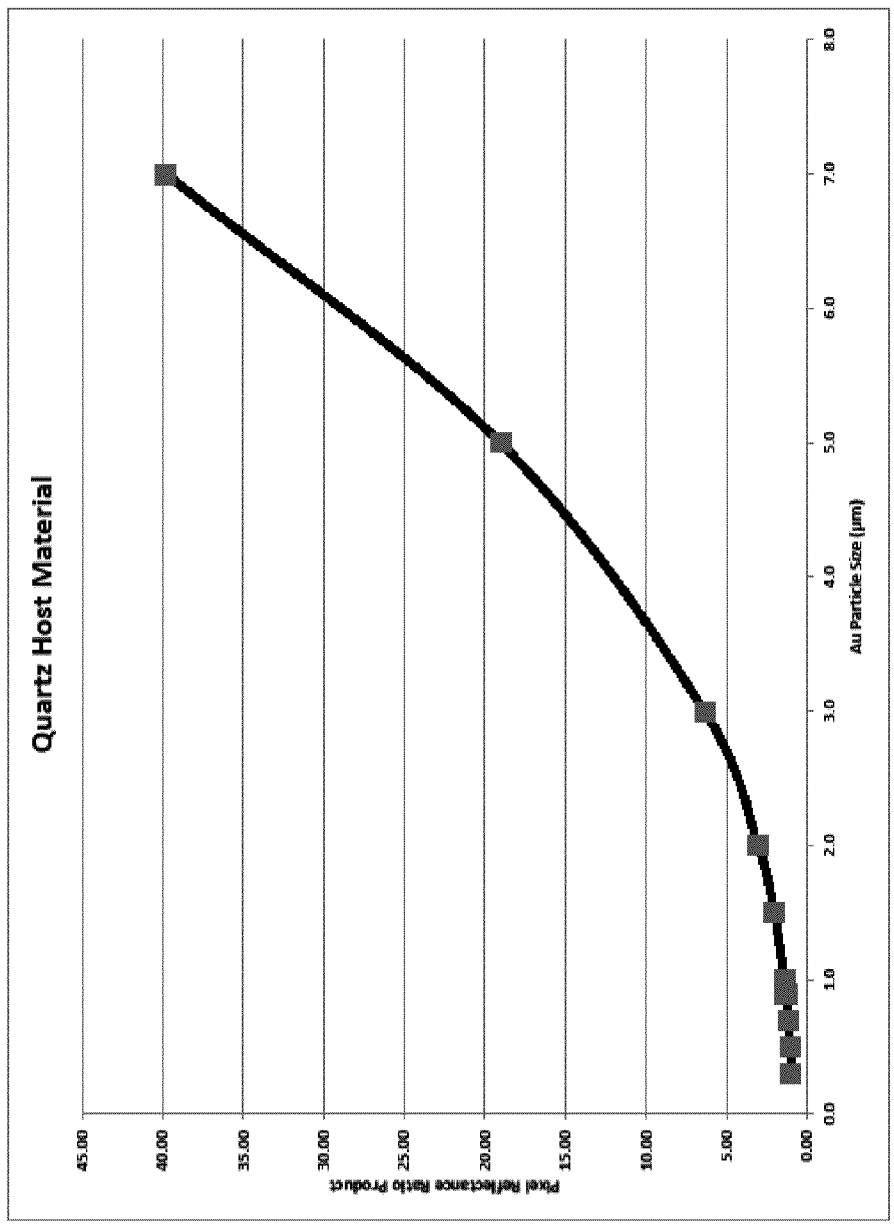
FIG. 2G is an exemplary plot of Reflectance Ratio Product against gold particle diameter for gold hosted in quartz.

Referring now to FIG. 1C, there is shown a graph of optical reflectance as a function of wavelength for three metals: gold (Au), silver (Ag) and aluminum (Al). A steep change in reflectance for gold at approximately 500 nm can be observed. A similar change in reflectance can also be observed for silver at about 325 nm, in the ultraviolet spectrum. However, the optical reflectance for aluminum remains relatively constant at all the wavelengths depicted. The principles of relativistic quantum chemistry that give rise to the reflectance characteristics displayed in FIG. 1C are known in the art.

These reflectance properties can be similar in an alloy, such as a gold and silver alloy, which often occurs in nature. There is no chemical bond between the gold and silver in such an alloy. In the absence of chemical bonds, the behavior of the respective outer electron orbitals of the atoms in the alloy is unchanged. Accordingly, the optical reflectance properties of the respective atoms are also unchanged.

500 nm. Gold-silver alloys may also be detected using similar techniques. Native silver may be more difficult to detect, as it may be tarnished with an oxide and/or sulphide coating and be relatively unreflective.

Table 1 provides reflectance values measured using optical techniques for a variety of materials—including gold, pyrite, chalcopyrite, arsenopyrite, pyrrhotite, sphalerite, galena and quartz—in a range of wavelengths between 400-700 nm.

TABLE 1

| Wavelength (nm) | Gold | Pyrite | Chalcopyrite R1 | Chalcopyrite R2 | Arsenopyrite R1 | Arsenopyrite R2 | Pyrrhotite R1 | Pyrrhotite R2 | Sphalerite | Galena | Quartz |
|---|---|---|---|---|---|---|---|---|---|---|---|
| 400 | 24.9 | 38.2 | 12.6 | 14.8 | 49.9 | 53 | 27.9 | 31 | 18.4 | 52.8 | 4.8 |
| 405 | 25.3 | 38.78 | 13.53 | 15.6 | 49.73 | 53 | 28.08 | 31.3 | 18.35 | 52.23 | 4.79 |
| 420 | 26.5 | 40.5 | 16.3 | 18 | 49.2 | 53 | 28.6 | 32.2 | 18.2 | 50.5 | 4.76 |
| 440 | 28.1 | 42.8 | 20 | 21.2 | 48.5 | 53 | 29.4 | 33.6 | 18 | 48.2 | 4.75 |
| 460 | 31.6 | 45.5 | 23.6 | 25 | 48.3 | 53 | 30.3 | 34.8 | 17.7 | 46.4 | 4.69 |
| 480 | 39 | 48.5 | 27 | 28.6 | 48.5 | 52.8 | 31.4 | 36.2 | 17.4 | 45 | 4.67 |
| 500 | 49.5 | 51 | 30.2 | 31.7 | 48.9 | 52.7 | 32.4 | 37.6 | 17.1 | 43.9 | 4.64 |
| 520 | 57.8 | 53.6 | 33 | 34.3 | 49.4 | 52.4 | 33.4 | 38.6 | 16.8 | 43 | 4.6 |
| 540 | 63.4 | 53.8 | 35.1 | 36.4 | 49.7 | 52 | 34.5 | 39.6 | 16.6 | 42.4 | 4.58 |
| 560 | 67.8 | 54.6 | 36.8 | 38 | 50.2 | 51.6 | 35.5 | 40.4 | 16.5 | 41.9 | 4.55 |
| 580 | 71 | 55 | 38.2 | 39.3 | 50.5 | 51.3 | 36.5 | 41.2 | 16.4 | 41.6 | 4.54 |
| 600 | 73.8 | 55.2 | 39.3 | 40.4 | 50.8 | 51.1 | 37.4 | 42 | 16.3 | 41.5 | 4.53 |
| 620 | 76.1 | 55.5 | 40.1 | 41 | 51 | 50.8 | 38.3 | 42.6 | 16.2 | 41.6 | 4.52 |
| 635 | 77.68 | 55.88 | 40.55 | 41.45 | 51.08 | 50.73 | 38.9 | 42.9 | 16.2 | 41.75 | 4.52 |
| 640 | 78.2 | 56 | 40.7 | 41.6 | 51.1 | 50.7 | 39.1 | 43 | 16.2 | 41.8 | 4.52 |
| 660 | 80.1 | 56.4 | 41.1 | 41.9 | 51.1 | 50.6 | 39.9 | 43.5 | 16.1 | 41.9 | 4.52 |
| 680 | 81.9 | 56.8 | 41.4 | 42 | 51.1 | 50.5 | 40.7 | 43.9 | 16 | 42.1 | 4.51 |
| 700 | 83.6 | 57 | 41.4 | 41.8 | 51 | 50.5 | 41.4 | 44.1 | 15.9 | 42.2 | 4.5 |

However, in practice, the reflectance properties of a gold and silver alloy will have a reflectance transition point at a wavelength that is intermediate between the 325 nm rise for silver and the 500 nm rise for gold. The precise transition point will depend on the relative quantities of the respective constituent metals. A higher concentration of gold will result in a transition closer to the 500 nm transition point of gold. Conversely, a lower concentration of gold will result in a transition closer to the 325 nm transition point of silver. Typically gold and silver alloys predominately consist of gold. Accordingly, the rise is likely to be at a higher wavelength (e.g., in the 450 nm to 500 nm range).

By taking advantage of these optical reflectance properties, even small gold particles can be detected using the techniques described herein. As long as a gold particle, however small, is close enough to the face of a mineral or material sample (e.g., a cleaved rock face) to reflect light, then its characteristic reflectance properties should be detectable.

In particular, by comparing the optical reflectance properties for a mineral or material sample when exposed to wavelengths in the BV range to the properties when exposed to wavelengths in the ROY range, gold and gold-silver alloys can be readily distinguished from other metals and minerals. It will be understood that a mineral sample need not be comprised entirely of a single mineral and may comprise other materials.

For example, if a ROY light source is chosen with a wavelength of 700 nm (red) and directed at a gold particle, the reflectance will be approximately 84%. If a BV light source is chosen with a wavelength of 400 nm (violet) and directed at the gold particle, the reflectance will be approximately 25%. Accordingly, the ratio of the gold particle's reflectance at the different wavelengths is 84% divided by 25%, or approximately 3.4

In general, to detect gold, the ROY light source should be chosen to have a wavelength of greater than 500 nm and the BV light source should be chosen to have a wavelength of less than about 500 nm, and preferably in the range of 325 nm to In some cases, multiple forms of a material may be present in a sample. For example, there may be equal parts of arsenopyrite R1 and arsenopyrite R2. Accordingly, to obtain the reflectance for the mixture, the reflectance value for each constituent component at the particular wavelength may be averaged. In most cases, gold particles will occur embedded in a mineral or other material sample among one or more minerals and other materials. Accordingly, the overall or average reflectance of the entire mineral or material sample may not exhibit the properties particular to gold. Reliably and efficiently detecting small particles of gold in such a sample may therefore require obtaining an array of localized reflectance measurements.

In some embodiments, the array of measurements can be obtained by using an image sensor, such as a complementary metal oxide semiconductor (CMOS) active pixel sensor device, or a charge-coupled device (CCD) image sensor. Such image sensors typically comprise a two-dimensional grid or array of photosensitive elements, which are used to generate a two-dimensional raster image, which comprises a corresponding grid. The raster image comprises a plurality of pixels corresponding to each point on the grid.

By directing substantially monochromatic light at a mineral sample (or by filtering images for particular desired wavelengths of light), and using a suitable image sensor to image the mineral sample while exposed to the monochromatic light, a relatively large array of reflectance sample points can be obtained in an efficient manner. In particular, an image sensor may comprise a two-dimensional matrix of sensor elements, yielding a large number of individual sample points. The individual sample points will correspond to pixels in an image generated by the image sensor. Pixels in the resulting image that appear "bright" can be interpreted as having a high average ROY reflectance, whereas pixels that appear dark may have a low average ROY reflectance.

In some embodiments, the sensor elements may comprise two or more sub-elements. For example, a color-sensitive sensor element may comprise two or more sub-elements that are sensitive to specific wavelength ranges of light. Alternatively, the sensor element may comprise two or more sub-elements that are provided with filters that correspond to specific wavelength ranges of light (e.g., red, blue, etc.).

Accordingly, the reflectance sample points obtained in this way can be compared against known reflectance values, such as shown in Table 1, to generally classify the materials that appear in the image. For example, a pixel that is dark when exposed to light with a wavelength of 700 nm can be ruled out as corresponding to gold.

By taking multiple exposures of a mineral sample when exposed to different wavelengths of light, desired reflectance characteristics as a function of wavelength can be identified.

For example, in some embodiments two or more light sources are used. Laser light sources are suitable because they can produce substantially monochromatic light at a desired wavelength. A first laser, emitting violet light at approximately 400 nm can be used to illuminate an area (e.g., one square centimeter) of the mineral sample and a first image captured of the light reflected by the material sample. The process may be repeated with a second laser emitting red light at approximately 650 nm. Using a color sensor element with filters over the elements that transmit only red or blue-violet light, the red and violet light can be detected simultaneously by the red-filtered element and blue-violet-filtered element respectively, in a color sensor element.

In some embodiments, the mineral sample is shielded from external light. However, if shielding is not absolute, or to improve accuracy, a third image may also be captured without illumination by either the first or second laser light source, to serve as a reference image.

The captured images can be processed and compared on a pixel-by-pixel basis to analyze the reflectance as a function of wavelength. Individual pixels in each of the captured images can be aligned to correspond to the same point of the mineral sample. Accordingly, differences in the brightness of the aligned pixels can be compared and used to identify the presence of gold or other materials.

Figure 4:
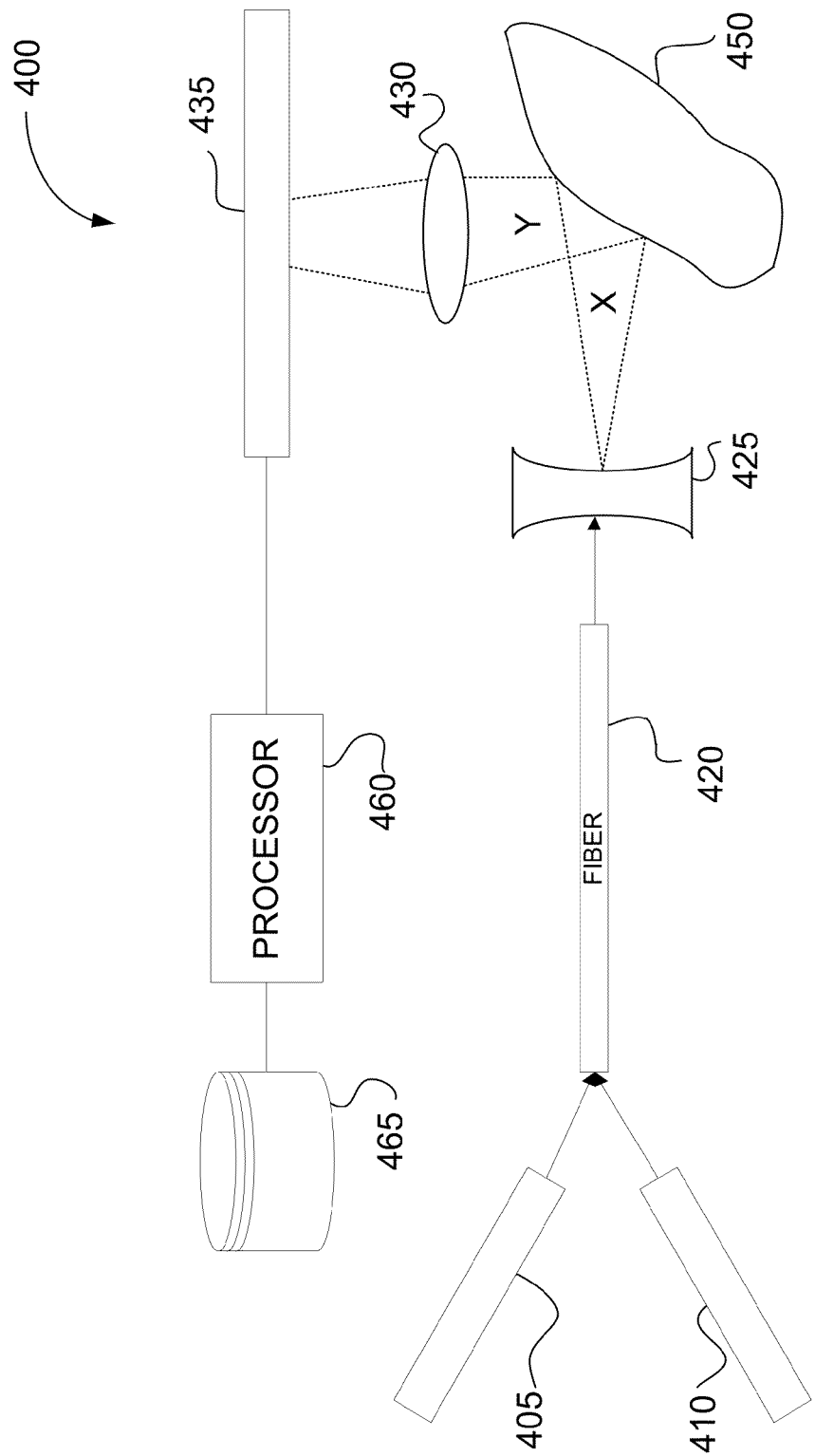
FIG. 4 is a schematic diagram of an exemplary apparatus in accordance with some embodiments.

To detect particular materials, such as gold, a weighted intensity value may be calculated for each pixel. In some embodiments, the weighted intensity value may comprise a Wavelength Reflectance Ratio (WRR). The Wavelength Reflectance Ratio may be a simple ratio of the pixel brightness in the first image (e.g., under ROY light) versus the pixel brightness in the second image (e.g., under BV light). Equation (1) can be used when the ROY and BV light intensities that are emitted from the optical fiber 420 in FIG. 4 are arranged to be equal so that the ROY and BV incident light intensities cancel when the ROY and BV reflectances are divided to calculate the Wavelength Reflectance Ratio. If the ROY and BV incident light intensities are not equal, then a factor equal to the ratio of the ROY and BV incident light intensities can be included in equation (1). In practice, the ROY and BV incident intensities can be set to be equal because this makes the calculation of WRR simpler. However, as noted, this does not need to be the case if a factor is introduced to account for the difference in ROY and BV incident intensities.

$$WRR = \frac{I_{roy}}{I_{bv}} \quad (1)$$

For a pixel occupied entirely by gold, the Wavelength Reflectance Ratio will have a value of approximately 3 if the intensity of the incident ROY and BV light is the same, and depending upon the specific wavelengths of ROY and BV light used. Due to its high reflectance for ROY light, a pixel with a significant fraction of its area occupied by gold is called a "bright pixel".

A Spatial Reflectance Ratio (SRR) can also be calculated for the bright pixels. The Spatial Reflectance Ratio can be the ROY reflectance for a bright pixel, which may be a candidate to contain gold, divided by the average ROY reflectance for all non-bright pixels in the image.

$$SRR = \frac{I_{roy}}{\overline{I_{roy}}} \quad (2)$$

The Spatial Reflectance Ratio for a particular pixel provides a measure of how bright that particular pixel is, or how much it "glitters" as compared to the host material.

For a pixel that captures only the host mineral, the SRR should be approximately 1, as the ROY reflectance will be the same or similar to the average of the ROY reflectance of the pixels containing host minerals.

The Wavelength Reflectance Ratio can be used to help discriminate gold from other reflective materials, such as sulphides, whose reflectance does not exhibit the large difference in reflectance between ROY and BV light.

In some embodiments, a product can be computed by multiplying the Wavelength Reflectance Ratio by the Spatial Reflectance Ratio. This product can be considered the "Reflectance Ratio Product" (RRP), which can serve as a useful indicator of whether gold is present in the area of the mineral surface corresponding to a given pixel. The measurement sensitivity of the Reflectance Ratio Product can make it possible to identify gold particles in the submicron and micron size range.

$$RRP = WRR \times SRR \quad (3)$$

For a pixel that captures only the host mineral, the WRR will be the ratio of the intensities at ROY and BV wavelengths for the host mineral, which can be more or less than 1. The SRR, as explained above, can be approximately 1. Accordingly, the RRP for the host mineral can be more or less than 1. Values of the RRP for a pixel filled with host mineral, and a pixel filled with host mineral and a gold particle, can be seen in Tables 2A to 2G herein. The percentage of the RRP for a pixel containing a gold particle above that of the RRP for a pixel containing only host mineral can also be seen.

As an example, using an image sensor with a resolution of 1920×1080 pixels (e.g., a total of 2,073,600 pixels), a single pass of the above-described technique can perform the equivalent of 2,073,600 measurements in parallel, as each pixel in the image corresponds to an individual measurement. If a single pixel corresponds to an area of 50 square microns of the mineral sample, an image comprising 2,073,600 pixels would correspond to approximately 1 square centimeter of the mineral sample. Commonly available CMOS and CCD image sensors have between ten to twenty million pixels. Detection resolution may also be expected to significantly improve with greater pixel capacity of image sensors, and with the ability to focus the image on smaller areas.

Typical gold grades encountered in the field can be of the order of 1 part per million. Thus, performing millions of measurements in parallel may enable gold to be detected, if present, with only a few imaging steps.

Gold particles may be detectable even if they do not fill an entire pixel of the resulting image. The reflectance properties of the gold may be "muted" by the surrounding material, but the overall reflectance for the pixel may be sufficient to facilitate detection. For example, given a pixel size corresponding to 50 square microns of the mineral sample, even gold particles in the submicron range may still provide a detectable increase in the Reflectance Ratio Product for that pixel.

Tables 2A to 2G describe the effect of gold particle size on a calculated Reflectance Ratio Product in a variety of materials, given a pixel area corresponding to 50 square microns of the mineral sample. Gold particles were modeled as a circle, and the measured reflectance data as a function of wavelength for gold and a variety of host minerals is tabulated, along with the computed reflectance ratios and products.

Pixels containing a gold particle can exhibit a Reflectance Ratio Product that exceeds that of pixels containing only the host material. A detection threshold may be used to eliminate spurious detections and false positives. For example, the detection threshold may be specified to require a 10% higher Reflectance Ratio Product than the known or measured Reflectance Ratio Product of the host material.

Using the criterion that the Reflectance Ratio Product for a pixel containing a gold particle must exceed the Reflectance Ratio Product for a pixel containing only the host mineral by 10%, Table 2A illustrates that a gold particle 2.3 microns in diameter can be detected in pyrite host material. For unreflective host minerals like quartz, shown in Table 2G, particles as small as 0.5 microns in diameter can be detected.

TABLE 2A

Pyrite Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 38.76 | 55.91 | 1.44 | 1.00 | 1.44 | 1.44 | 0% |
| 0.5 | 0.39 | 38.72 | 55.96 | 1.45 | 1.00 | 1.45 | 1.44 | 1% |
| 0.7 | 0.77 | 38.67 | 56.04 | 1.45 | 1.00 | 1.45 | 1.44 | 1% |
| 0.9 | 1.27 | 38.60 | 56.15 | 1.45 | 1.00 | 1.46 | 1.44 | 1% |
| 1.0 | 1.57 | 38.56 | 56.22 | 1.46 | 1.01 | 1.47 | 1.44 | 2% |
| 2.0 | 6.28 | 37.93 | 57.24 | 1.51 | 1.02 | 1.55 | 1.44 | 8% |
| 3.0 | 14.14 | 36.87 | 58.96 | 1.60 | 1.06 | 1.69 | 1.44 | 17% |
| 5.0 | 39.27 | 33.48 | 64.44 | 1.92 | 1.15 | 2.22 | 1.44 | 54% |
| 7.0 | 76.97 | 28.40 | 72.65 | 2.56 | 1.30 | 3.33 | 1.44 | 131% |

TABLE 2B

Chalcopyrite Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 14.58 | 41.05 | 2.82 | 1.00 | 2.82 | 2.82 | 0% |
| 0.5 | 0.39 | 14.60 | 41.14 | 2.82 | 1.00 | 2.83 | 2.82 | 0% |
| 0.7 | 0.77 | 14.65 | 41.28 | 2.82 | 1.01 | 2.84 | 2.82 | 1% |
| 0.9 | 1.27 | 14.70 | 41.47 | 2.82 | 1.01 | 2.85 | 2.82 | 1% |
| 1.0 | 1.57 | 14.73 | 41.58 | 2.82 | 1.01 | 2.86 | 2.82 | 1% |
| 2.0 | 6.28 | 15.24 | 43.30 | 2.84 | 1.06 | 3.00 | 2.82 | 6% |
| 3.0 | 14.14 | 16.08 | 46.18 | 2.87 | 1.13 | 3.24 | 2.82 | 15% |
| 5.0 | 39.27 | 18.78 | 55.40 | 2.95 | 1.35 | 3.99 | 2.82 | 41% |
| 7.0 | 76.97 | 22.83 | 69.23 | 3.03 | 1.69 | 5.12 | 2.82 | 82% |

TABLE 2C

Arsenopyrite Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 51.33 | 50.94 | 0.99 | 1.00 | 0.99 | 0.99 | 0% |
| 0.5 | 0.39 | 51.26 | 51.01 | 1.00 | 1.00 | 1.00 | 0.99 | 1% |
| 0.7 | 0.77 | 51.16 | 51.11 | 1.00 | 1.00 | 1.00 | 0.99 | 1% |
| 0.9 | 1.27 | 51.03 | 51.24 | 1.00 | 1.01 | 1 01 | 0.99 | 2% |
| 1.0 | 1.57 | 50.95 | 51.32 | 1.01 | 1.01 | 1.02 | 0.99 | 3% |
| 2.0 | 6.28 | 49.72 | 52.58 | 1.06 | 1.03 | 1.09 | 0.99 | 10% |
| 3.0 | 14.14 | 47.68 | 54.69 | 1.15 | 1.07 | 1.23 | 0.99 | 24% |
| 5.0 | 39.27 | 41.13 | 61.41 | 1.49 | 1.21 | 1.80 | 0.99 | 82% |
| 7.0 | 76.97 | 31.30 | 71.51 | 2.28 | 1.40 | 3.21 | 0.99 | 224% |

TABLE 2D

Pyrrhotite Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 29.68 | 40.95 | 1.38 | 1.00 | 1.38 | 1.38 | 0% |
| 0.5 | 0.39 | 29.67 | 41.04 | 1.38 | 1.00 | 1.39 | 1.38 | 1% |
| 0.7 | 0.77 | 29.65 | 41.18 | 1.39 | 1.01 | 1.40 | 1.38 | 1% |
| 0.9 | 1.27 | 29.63 | 41.37 | 1.40 | 1.01 | 1.41 | 1.38 | 2% |
| 1.0 | 1.57 | 29.62 | 41.48 | 1.40 | 1.01 | 1.42 | 1.38 | 3% |
| 2.0 | 6.28 | 29.41 | 43.21 | 1.47 | 1.06 | 1.55 | 1.38 | 12% |
| 3.0 | 14.14 | 29.07 | 46.10 | 1.59 | 1.13 | 1.79 | 1.38 | 30% |
| 5.0 | 39.27 | 27.96 | 55.34 | 1.98 | 1.35 | 2.68 | 1.38 | 94% |
| 7.0 | 76.97 | 26.31 | 69.21 | 2.63 | 1.69 | 4.45 | 1.38 | 222% |

TABLE 2E

Sphalerite Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 18.36 | 16.29 | 0.89 | 1.01 | 0.89 | 0.88 | 1% |
| 0.5 | 0.39 | 18.38 | 16.44 | 0.89 | 1.01 | 0.91 | 0.88 | 3% |
| 0.7 | 0.77 | 18.40 | 16.67 | 0.91 | 1.03 | 0.93 | 0.88 | 6% |
| 0.9 | 1.27 | 18.44 | 16.98 | 0.92 | 1.05 | 0.97 | 0.88 | 10% |
| 1.0 | 1.57 | 18.46 | 17.17 | 0.93 | 1.06 | 0.99 | 0.88 | 13% |
| 2.0 | 6.28 | 18.79 | 20.06 | 1.07 | 1.24 | 1.32 | 0.88 | 50% |
| 3.0 | 14.14 | 19.33 | 24.89 | 1.29 | 1.54 | 1.98 | 0.88 | 125% |
| 5.0 | 39.27 | 21.08 | 40.34 | 1.91 | 2.49 | 4.77 | 0.88 | 442% |
| 7.0 | 76.97 | 23.70 | 63.52 | 2.68 | 3.92 | 10.51 | 0.88 | 1094% |

TABLE 2F

Galena Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 52.19 | 41.80 | 0.80 | 1.00 | 0.80 | 0.80 | 0% |
| 0.5 | 0.39 | 52.12 | 41.89 | 0.80 | 1.00 | 0.81 | 0.80 | 1% |
| 0.7 | 0.77 | 52.02 | 42.03 | 0.81 | 1.01 | 0.81 | 0.80 | 1% |
| 0.9 | 1.27 | 51.88 | 42.21 | 0.81 | 1.01 | 0.82 | 0.80 | 3% |
| 1.0 | 1.57 | 51.80 | 42.31 | 0.82 | 1.01 | 0.83 | 0.80 | 4% |
| 2.0 | 6.28 | 50.53 | 44.01 | 0.87 | 1.05 | 0.92 | 0.80 | 15% |
| 3.0 | 14.14 | 48.42 | 46.83 | 0.97 | 1.12 | 1.08 | 0.80 | 35% |
| 5.0 | 39.27 | 41.65 | 55.86 | 1.34 | 1.34 | 1.79 | 0.80 | 124% |
| 7.0 | 76.97 | 31.50 | 69.40 | 2.20 | 1.66 | 3.66 | 0.80 | 358% |

TABLE 2G

Quartz Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 0.3 | 0.14 | 4.82 | 4.62 | 0.96 | 1.02 | 0.98 | 0.94 | 4% |
| 0.5 | 0.39 | 4.87 | 4.81 | 0.99 | 1.06 | 1.05 | 0.94 | 12% |
| 0.7 | 0.77 | 4.95 | 5.08 | 1.03 | 1.12 | 1.16 | 0.94 | 23% |
| 0.9 | 1.27 | 5.05 | 5.45 | 1.08 | 1.21 | 1.30 | 0.94 | 38% |
| 1.0 | 1.57 | 5.11 | 5.67 | 1.11 | 1.25 | 1.39 | 0.94 | 48% |
| 1.5 | 3.53 | 5.51 | 7.11 | 1.29 | 1.57 | 2.03 | 0.94 | 116% |
| 2.0 | 6.28 | 6.08 | 9.12 | 1.50 | 2.02 | 3.02 | 0.94 | 221% |

TABLE 2G-continued

Quartz Host Material

| Au Particle Size (μm) | Au Particle Size/Pixel Size (%) | Pixel Reflectance @ 405 nm (%) | Pixel Reflectance @ 635 nm (%) | Wavelength Reflectance Ratio | Spatial Reflectance Ratio | Pixel Reflectance Ratio Product | Host Material Reflectance Ratio Product | Percent Above Host Material RRP |
|---|---|---|---|---|---|---|---|---|
| 3.0 | 14.14 | 7.69 | 14.86 | 1.93 | 3.29 | 6.36 | 0.94 | 577% |
| 5.0 | 39.27 | 12.84 | 33.25 | 2.59 | 7.36 | 19.04 | 0.94 | 1926% |

Accordingly, pixel-by-pixel comparison of the Reflectance Ratio Product may permit the identification of gold particles on the scale of microns.

In many cases, gold is likely to be present in only trace quantities. As several million pixels can be measured at once using an image sensor, and as gold is likely to be present in only a few pixels, the pixels that do not initially exhibit one or more reflectance properties of gold can be used to provide a large sample of the reflectance properties of the host material. The reflectance properties of the host material can be estimated by computing an average reflectance of the non-bright pixels that do not appear to contain gold.

Accordingly, in a first stage of analysis, the reflected ROY light intensity of each pixel can be measured and compared to the average ROY light intensity reflected by all pixels (e.g., Spatial Reflectance Ratio). The Spatial Reflectance Ratio can be considered as a measurement that detects bright pixels that are likely to contain gold.

In a further stage, for pixels with higher than average reflectance of ROY light (e.g., bright pixels), the Wavelength Reflectance Ratio for these pixels can be computed (e.g., for ROY light to BV light). Depending on the specific ROY and BV wavelengths used, the ratio will be approximately 3 if the pixel is entirely occupied by gold.

Figure 3A:
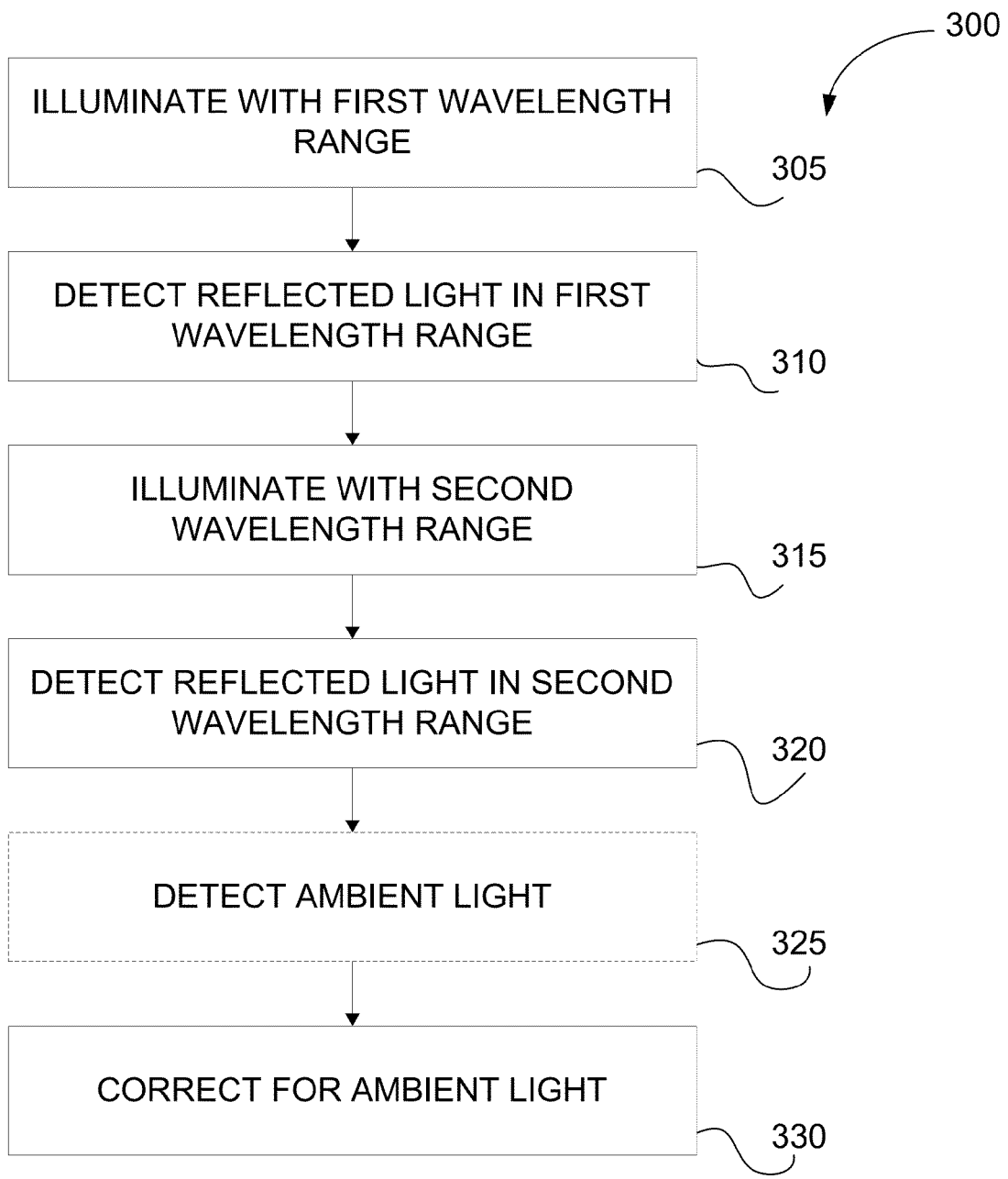
FIG. 3A is an exemplary flow diagram of a gold detection process in accordance with some embodiments.

Referring now to FIG. 3A, there is shown an exemplary flow diagram of a detection process in accordance with some embodiments.

Detection process 300 begins at 305 by illuminating a material sample with a first preselected wavelength range of light. The light can be directed such that it reflects from a desired surface of the mineral sample, and the reflected light can be detected at 310, for example by an image sensor to produce a first image.

Similarly, at 315, the material sample can be illuminated with a second preselected wavelength range of light. The light can again be directed such that it reflects from a desired surface of the mineral sample, and the reflected light can be detected at 320, again for example by an image sensor to produce a second image.

The first preselected wavelength range of light may be in the BV spectrum and the second preselected wavelength range of light may be in the ROY spectrum, although it will be appreciated that these may be reversed.

In some embodiments, 305 and 315 may be performed substantially simultaneously. For example, rather than using separate light sources, each producing a distinct wavelength range of light (e.g., monochromatic lasers), a broad spectrum light source can be used to produce a wide wavelength range of light, comprising both the first and second wavelength ranges. Accordingly, the material sample can be illuminated with both ranges simultaneously. In order to detect the first and second wavelength ranges separately, first and second filter elements may be used to isolate the first and second wavelength ranges, respectively.

For example, 305 and 315 may be performed substantially simultaneously using monochromatic light produced by lasers that are projected together, and detected together on a color pixel containing elements with color filters that permit one element to detect only ROY light and the other to detect only BV light. Such an arrangement can be seen in FIG. 4 where the ROY and BV light can be simultaneously coupled into an optical fiber and then emitted together from the core of the optical fiber, and in FIG. 5 where the ROY and BV light are detected simultaneously by a color pixel with a red filter over one element and a blue filter over another element. These filters can have approximately 50 nm bandwidths and thus the filter materials can be selected to transmit the ROY and BV light through each of their respective filters.

Alternatively, 305 and 315 may be performed sequentially, in which case the color filters may not be required.

Optionally, at 325, the at least one light source may be disabled and ambient light may be detected to generate a reference image. At 330, the images or data may be processed to eliminate the effect of ambient light.

Figure 3B:
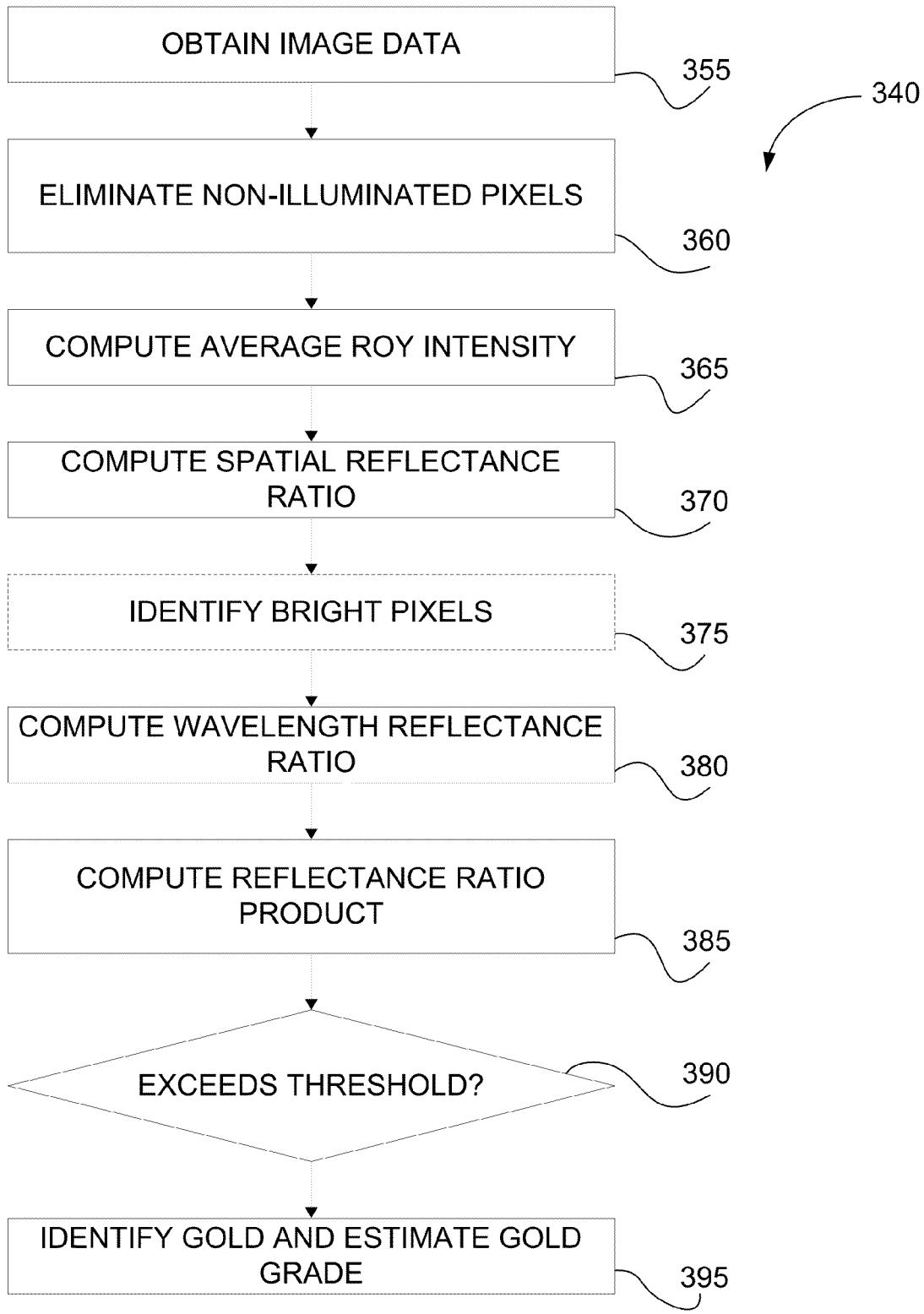
FIG. 3B is an exemplary flow diagram of a signal processing algorithm in accordance with some embodiments.

Referring now to FIG. 3B, there is shown an exemplary flow diagram of a signal processing algorithm that may be carried out by a processor in some embodiments to analyze intensity and relative reflectance data.

Analysis process 340 begins at 355, by retrieving image data from the image sensors. The image data can comprise a ROY image and a BV image, where each image is generated by exposing a sample to substantially monochromatic light at a suitable wavelength (e.g., 635 nm for ROY and 405 nm for BV).

At 360, the processor can discard or ignore pixels with a reflected light intensity that is below a predetermined exposure threshold value. The predetermined exposure threshold value can be used to discard image data that is underexposed or unexposed, for example where an area of the sample was not illuminated by a light source.

The average ROY light intensity for the ROY image can be computed at 365 by averaging the reflected light intensity of each illuminated pixel (e.g., each pixel that was not discarded at 360). The average ROY light intensity can be further refined by eliminating pixels from the average whose ROY light intensity exceeds the first calculated average by a predetermined amount (e.g. 10%). This provides an average ROY light intensity for pixels that are unlikely to contain gold.

A normalized ROY light intensity called the Spatial Reflectance Ratio (SRR) for each pixel in the ROY image can be computed at 370 by dividing each pixel's ROY light intensity by the average ROY light intensity, as computed at 365.

Pixels with a Spatial Reflectance Ratio that exceeds a minimum threshold can be selected at 375. For example, the processor may identify those pixels whose Spatial Reflectance Ratio exceeds the average Spatial Reflectance Ratio by a predetermined amount or percentage (e.g., 10%). The identified pixels may be considered as "bright pixels".

For each of the pixels the processor can divide the ROY light intensity for the pixel by the BV light intensity for the pixel at 380, to compute the Wavelength Reflectance Ratio (WRR) for the pixel.

At 385, the value of the Reflectance Ratio Product (RPP) for each pixel may be computed by multiplying the Wavelength Reflectance Ratio (WRR) by the Spatial Reflectance Ratio (SRR) as specified by equation (3).

A Reflectance Ratio Product for a bright pixel greater by a certain amount (e.g. 10%) than the average Reflectance Ratio Product for non-bright pixels, may indicate the presence of gold in a given bright pixel.

Based on the Reflectance Ratio Product value, the processor may determine whether gold is present in a given pixel at 390. If gold is present, the Wavelength Reflectance Ratio may further be used to estimate the diameter of the gold particle or particles in each bright pixel at 395. This can be done using equation (4):

$$x = \frac{WRR * R_{HBV} - R_{HROY}}{WRR * (R_{HBV} - R_{AuBV}) + R_{AuROY} - R_{HROY}} \quad (4)$$

Where x is the fraction of the pixel covered by gold. $R_{HBV}$ can be the reflectance of the host mineral for the BV wavelength measured from the average BV reflected light intensity and the incident light intensity calculated from the laser light power, the area illuminated and the area of the pixel. $R_{HBV}$ can also be determined from tabulated data if the user is able to supply the type of host mineral.

$R_{HROY}$ can be the reflectance of the host mineral for the ROY wavelength measured from the average ROY reflected light intensity and the incident light intensity calculated from the laser light power, the area illuminated and the area of the pixel. $R_{HROY}$ can also be determined from tabulated data if the user is able to supply the type of host mineral.

$R_{AuBV}$ can be the reflectance for gold at the BV wavelength which is a known quantity. It can be adjusted to account for impurities such as silver or copper if the concentrations of these impurities are known for the sample from other techniques.

$R_{AuROY}$ can be the reflectance for gold at the ROY wavelength which is a known quantity. It can be adjusted to account for impurities such as silver or copper if the concentrations of these impurities are known for the sample from other techniques.

Using the fraction x of each bright pixel that is covered by gold, the fraction of the total analyzed mineral surface covered by gold (Gold Fraction) may be calculated. Assuming that the surface area density and volume density are the same, and correcting for the difference in density between gold, or the gold alloy that is present in a given sample, and the host mineral, the gold grade can be calculated from equation (5):

$$\text{Gold Grade} = \text{Gold Fraction} * \rho Au / \rho_{Host} \quad (5)$$

In some embodiments, if gold is suspected in a predetermined sample area, or if the result for a subarea of the sample is inconclusive, the desired area may be reimaged with optical magnification applied (e.g., using a zoom lens to focus on the desired area) and the process repeated, to obtain even greater resolution and detection sensitivity. With optical magnification applied, each pixel may correspond to an area of the mineral sample that is even smaller than 50 square microns, with the concomitant increase in detection sensitivity.

Using process 340, gold particles on the order of 1 micron in diameter can be detected, and at grades as low as 50 to 100 ppb, which can be as much as three orders of magnitude more sensitive than current analyzers.

This is because the gold sniffer can detect a circular gold particle whose diameter is 1 micron on a 1 square centimeter area of a mineral whose area is $10^8 \, \mu m^2$, and the density of naturally occuring gold alloy can be estimated to be 18 g/cm^3 (with impurities reducing its density from the 19.3 g/cm^3 density of pure gold) and the density of a typical host mineral is 2.7 g/cm^3. Therefore the minimum detectable gold grade can be estimated as:

$$\frac{\pi * 1^2}{4 * 10^8} * \frac{18}{2.7} = 52 \, ppb \quad (6)$$

Typical gold grade detection limits for portable XRF detectors are in the range of 50 parts per million (ppm) in the field, and approximately 5 ppm under carefully calibrated lab conditions.

In some embodiments, additional signal processing techniques may also be employed, as will be appreciated. For example, image data may be enhanced using similar techniques to those used by astronomers to enhance CCD array pictures captured by telescopes of planets, stars, galaxies and nebulae.

Similar image processing methods can be used with the image of a mineral surface. This may permit the elimination or reduction of optical noise and stray reflections through image enhancement by the combination of multiple images, source discrimination, and the calculation of reflectance ratios and products that are obtained by dividing and multiplying the image data in multiple images.

In addition, more than two light wavelengths may be used, as noted above. The additional wavelengths can be used to further enhance the ability to discriminate for gold or other materials, if required.

In an alternative embodiment, three or more images may be generated. First and second images would correspond to ROY and BV illumination as described herein. However, a third image could be generated in which neither ROY nor BV illumination is used. Accordingly, image data from the third, unexposed image in particular can be used to enhance detection quality and sensitivity, for example, by eliminating "stuck" pixels that appear in all three images, to reduce noise, or to compensate for the presence of broad spectrum visible light.

Referring now to FIG. 4, there is shown an exemplary apparatus for detecting gold in accordance with some embodiments. Apparatus 400 comprises one or more light sources, for example, a first light source 405 and a second light source 410, which can be substantially monochromatic. In some embodiments, first light source 405 may be a ROY diode laser and second light source may be a BV diode laser. In other embodiments, there may be only a first light source 405, which produces broad spectrum light.

Examples of suitable light sources that are relatively inexpensive and readily available commercially include the indium gallium nitride (InGaN) diode lasers, such as those used in Blu-ray™ disc players, which produce light with a wavelength of 405 nm. Diode lasers such as those used in commercially-available red laser pointers can produce light with a wavelength of between 635 and 670 nm. In addition, diode lasers used in DVD™ players produce light with a wavelength of 657 nm.

The first and second light sources may be used substantially simultaneously or sequentially to illuminate a mineral sample 450 with two wavelengths of light. Light from each source may be directed to a desired area by, for example, an optical fiber 420. The light emitted from the optical fiber can be passed through a focusing lens element 425, which can be concave to spread the emitted light X over a desired area of the mineral sample 450. In some embodiments, the focusing lens element 425 may simply comprise the end of an optical fiber, as light emitted from an optical fiber may spread out from the end of the optical fiber enough to project light over a sample area of interest. Reflected light Y can be captured by another focusing lens element 430, which can be convex to focus the reflected light onto an image sensor 435.

Once an image is formed by image sensor 435, it can be transmitted to a processor 460 for further processing and/or storage in storage device 465. Processor 460 may be a general purpose processor, a field programmable gate array (FPGA) or other suitable processor, which can be programmed to perform the desired image processing.

Each of the components of apparatus 400 can be chosen to be small, light and to require low power. Accordingly, apparatus 400 can be constructed in a rugged, hand held enclosure, to act as a battery powered instrument, useful in the field for mineral exploration, and for grade control during gold mining. A hand held apparatus would require minimal training to use, and would be considerably safer to use than an X-Ray Fluorescence (XRF) detector. In particular, apparatus 400 employs only visible light and not high energy ionizing radiation such as X-rays. Apparatus 400 could be used safely with minimal precautions to avoid directing laser light into a user's eyes. In addition, safety features can be incorporated into the apparatus 400 to minimize the risk of laser injury, for example a proximity sensor to ensure that lasers are only enabled if a mineral sample is within a predetermined range of the apparatus. This can ensure that the laser light is not projected at a longer distance that could damage a bystander's eyes.

In some alternative embodiments, one or more broad spectrum light sources could be used instead of monochromatic light sources. The broad spectrum light can be filtered using two or more selective wavelength filter elements as desired to generate images that correspond to ROY and BV bandwidths of light.

Figure 5:
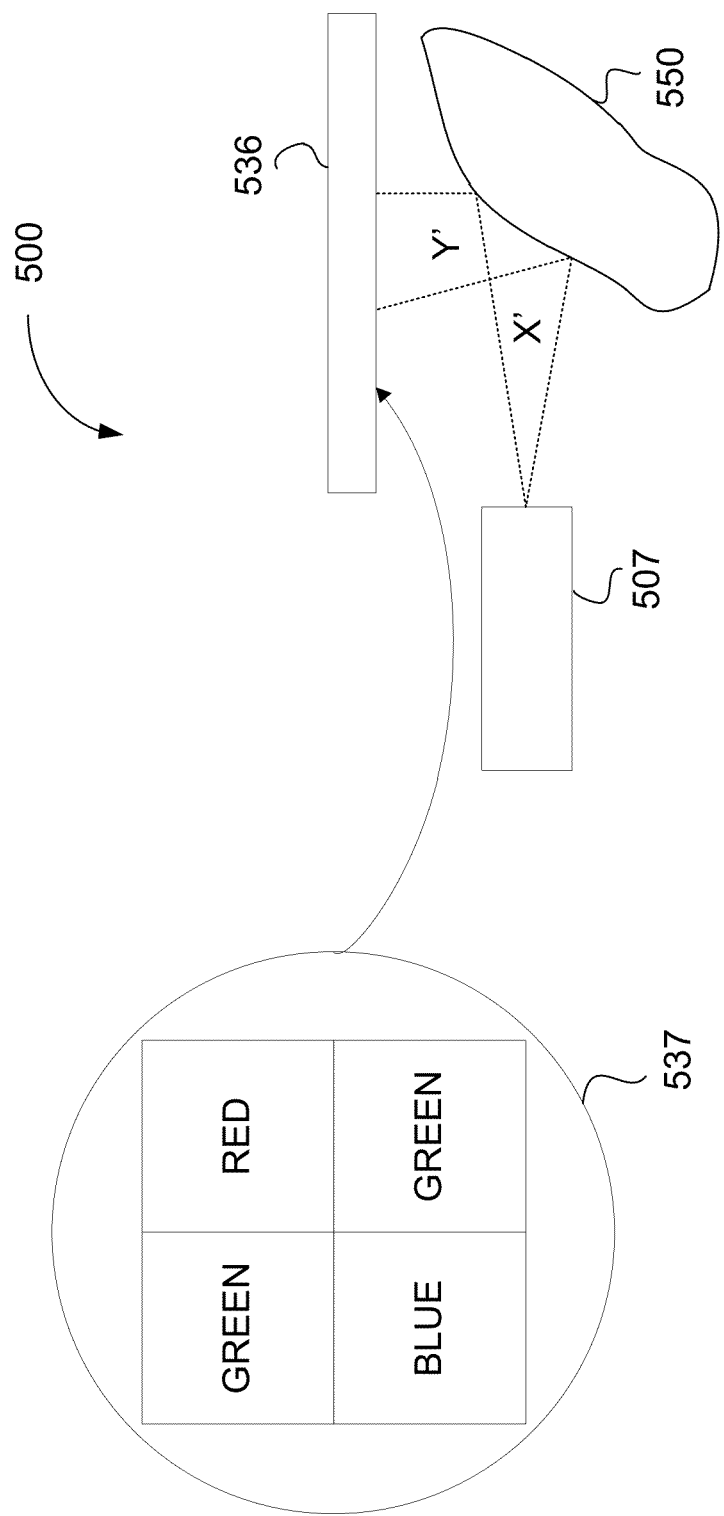
FIG. 5 is a schematic diagram of another exemplary apparatus in accordance with some embodiments.

Referring now to FIG. 5, there is shown an exemplary schematic diagram of a detection apparatus in accordance with both the previously described monochromatic diode laser light sources, and an alternative embodiment using broad spectrum light sources. As previously described, when using ROY and BV monochromatic diode laser light sources, the ROY and BV light can be detected by the color pixel simultaneously. This can be accomplished using the red and blue filters over their respective sensor elements. The red filter transmits only the ROY light, and the blue filter transmits only the BV light. Therefore the ROY and BV light can be detected simultaneously by the color pixel without interfering with each other.

Alternatively, if a single white light source is projected and reflected off a mineral sample, and detected by a color sensor array, then the red and blue light can be filtered by the color sensor elements, and may be used to generate the desired images for carrying out process 300.

Accordingly, apparatus 500 can comprise a broad spectrum light source 507, which projects light X' onto a mineral sample 550. Reflected light Y' can be detected by image sensor 536, which in this case is a color array. The image sensor may have color filter elements 537, which generate the desired reflectance image.

The color filter approach can have the advantage that it is relatively simple and inexpensive to produce. For example, the color filter in a color pixel may be patterned lithographically over the sensor elements during the fabrication process. However, accuracy may be reduced, since the red and blue filters in an element may admit light in approximately a 50 nm bandwidth range. In contrast, the bandwidth of a diode laser may be only a few nanometers. The wider bandwidth of the filtered light may result in diminished detection capability for the sharp change in the reflectance characteristic of gold at 500 nm. Accordingly, this may result in a larger minimum gold particle size that can be identified and a higher minimum gold grade that can be measured.

As white light sources are generally considerably more diffuse than laser sources, no lenses are required in apparatus 500. However, if desired, both convex and concave lenses may also be used in a similar manner as in apparatus 400.

Referring now to FIG. 6, there is shown a diagram of an exemplary portable enclosure for a detection apparatus, such as apparatus 400 or 500. Enclosure 600 can be provided in a "pistol-grip" or other suitable enclosure.

Enclosure 600 can comprise a handle 685, a trigger actuator 690 for activating various functions of the apparatus (e.g., capturing images for detection), a control panel 665, display 670 for interacting with software in the apparatus to configure various settings, a speaker 675 to provide an audible signal for the detection of gold, an on/off switch 680, a flexible seal 660 for covering a mineral sample under examination, to block out unwanted light, and an antenna 695, which may be used for wireless communication of, for example, detection data.

Display 670 may display information regarding gold grade, gold particle size and other information. Likewise, control panel 665 may provide settings for the operation of the apparatus, such as customized analysis programs for particular host minerals. In some embodiments, display 670 and control panel 665 may be combined in a touch screen device.

For ease of exposition, embodiments are described herein primarily with reference to gold detection. However, it will be understood that the methods described herein may also be applicable to the detection of other metals or materials exhibiting a desired optical reflectance characteristic as a function of wavelength.

Some of the embodiments of the systems and methods described herein may be implemented in hardware, or a combination of hardware and software. In particular, aspects of the embodiments comprising software may be implemented in computer programs executing on programmable computers, which may comprise at least one processor, a data storage system (including volatile and non-volatile memory and/or storage elements) and a display. For example and without limitation, the programmable computers may be an embedded device, personal computer, laptop, personal data assistant or mobile device. Program code is applied to input data to perform the functions described herein and generate output information. The output information is applied to one or more output devices, such as a display, in known fashion. Each such computer program is preferably stored on a non-transitory computer readable storage medium.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Various modifications and variations may be made to these exemplary embodiments without departing from the scope of the invention, which is limited only by the appended claims.

The invention claimed is:

1. A method for detecting gold in a material sample, the method comprising:
   a) illuminating the material sample with light in a first preselected wavelength range less than 500 nm and with light in a second preselected wavelength range greater than 500 nm;
   b) detecting the light in the first preselected wavelength range reflected by the material sample and the light in the second preselected wavelength range reflected by the material sample, wherein the light is detected by an image sensor comprising a two-dimensional matrix of sensor elements; and
   c) computing, using a processor, a reflectance ratio product for each individual sensor element in the two-dimensional matrix of sensor elements, wherein the reflectance ratio product comprises the product of a wavelength reflectance ratio and a spatial reflectance ratio, wherein the wavelength reflectance ratio comprises relative intensity of the reflected light in the second preselected wavelength range to the reflected light in the first preselected wavelength range, and wherein the spatial reflectance ratio is computed based on the ratio of relative intensity of the reflected light in the second preselected wavelength range in each individual sensor element to relative intensity of the reflected light in the second preselected wavelength range in a plurality of sensor elements.

2. The method of claim 1, wherein the material sample is substantially simultaneously illuminated in the first preselected wavelength range and in the second preselected wavelength range.

3. The method of claim 1, wherein the material sample is sequentially illuminated in the first preselected wavelength range and in the second preselected wavelength range.

4. The method of claim 1, wherein the first preselected wavelength range is in the BV spectrum, and wherein the second preselected wavelength range is in the ROY spectrum.

5. The method of claim 4, wherein the spatial reflectance ratio is the ratio of relative intensity of the reflected light in the second preselected wavelength range detected at each individual sensor element in the two-dimensional matrix of sensor elements to average relative intensity of the reflected light in the second preselected wavelength range detected at all sensor elements in the two-dimensional matrix of sensor elements.

6. The method of claim 1, wherein the reflected light is filtered to isolate the first preselected wavelength range, and wherein the reflected light is separately filtered to isolate the second preselected wavelength range.

7. The method of claim 1, further comprising detecting ambient light reflected by the material sample, wherein the detected ambient light reflected by the material sample is used to reduce noise when computing the relative intensity in c).

8. An apparatus for detecting gold in a material sample, the apparatus comprising:
   a) at least one light source for illuminating the material sample with light in a first preselected wavelength range less than 500 nm and with light in a second preselected wavelength range greater than 500 nm;
   b) an image sensor comprising a two-dimensional matrix of sensor elements for detecting the light in the first preselected wavelength range reflected by the material sample and the light in the second preselected wavelength range reflected by the material sample; and
   c) a processor for computing a reflectance ratio product for each sensor element in the two-dimensional matrix of sensor elements, wherein the reflectance ratio product comprises the product of a wavelength reflectance ratio and a spatial reflectance ratio, wherein the wavelength reflectance ratio comprises relative intensity of the reflected light in the second preselected wavelength range to the reflected light in the first preselected wavelength range, and wherein the spatial reflectance ratio is computed based on the ratio of relative intensity of the reflected light in the second preselected wavelength range in each individual sensor element to relative intensity of the reflected light in the second preselected wavelength range in a plurality of sensor elements.

9. The method of claim 7, wherein the spatial reflectance ratio is the ratio of relative intensity of the reflected light in the second preselected wavelength range detected at each individual sensor element in the two-dimensional matrix of sensor elements to average relative intensity of the reflected light in the second preselected wavelength range detected at all sensor elements in the two-dimensional matrix of sensor elements.

10. The apparatus of claim 8, wherein each sensor element comprises a first sub-element sensitive to the first preselected wavelength range and a second sub-element sensitive to the second preselected wavelength range.

11. The apparatus of claim 8, wherein the first preselected wavelength range is in the BV spectrum, and wherein the second preselected wavelength range is in the ROY spectrum.

12. The apparatus of claim 8, wherein the image sensor is configured to detect ambient light reflected by the material sample, and wherein the processor is configured to use the detected ambient light reflected by the material sample to reduce noise when computing the relative intensity.

13. The apparatus of claim 8, further comprising a first lens element, the first lens element for focusing light reflected by the material sample onto the image sensor.

14. The apparatus of claim 13, further comprising a second lens element, the second lens element for diffusing light from the at least one light source onto the material sample.

15. The apparatus of claim 14, wherein the second lens element is an end of an optical fiber.

16. The apparatus of claim 8, wherein the at least one light source comprises a first laser source for transmitting light in the first preselected wavelength range and a second laser source for transmitting light in the second preselected wavelength range.

17. The apparatus of claim 8, wherein the at least one light source is a broad spectrum light source, the apparatus further comprising a first filter element to filter the reflected light to isolate the first preselected wavelength range, and a second filter element to filter the reflected light to isolate the second preselected wavelength range.

18. The apparatus of claim 8, wherein the image sensor is selected from the group consisting of a CCD image sensor and a CMOS image sensor.

19. The apparatus of claim 8, further comprising a portable enclosure, the portable enclosure housing the at least one light source, the image sensor and the processor.

20. A non-transitory computer-readable storage medium with an executable program stored thereon, the executable program configured to instruct a processor to perform a method for detecting gold in a material sample, the method comprising:

a) illuminating the material sample with light in a first preselected wavelength range less than 500 nm and with light in a second preselected wavelength range greater than 500 nm;
b) detecting the light in the first preselected wavelength range reflected by the material sample and the light in the second preselected wavelength range reflected by the material sample, wherein the light is detected by an image sensor comprising a two-dimensional matrix of sensor elements; and
c) computing, using a processor, a reflectance ratio product for each individual sensor element in the two-dimensional matrix of sensor elements, wherein the reflectance ratio product comprises the product of a wavelength reflectance ratio and a spatial reflectance ratio, wherein the wavelength reflectance ratio comprises relative intensity of the reflected light in the second preselected wavelength range to the reflected light in the first preselected wavelength range, and wherein the spatial reflectance ratio is computed based on the ratio of relative intensity of the reflected light in the second preselected wavelength range in each individual sensor element to relative intensity of the reflected light in the second preselected wavelength range in a plurality of sensor elements.

* * * * *

UNITED STATES PATENT AND TRADEMARK OFFICE
CERTIFICATE OF CORRECTION

PATENT NO.       : 8,416,418 B2  
APPLICATION NO.  : 13/182871  
DATED            : April 9, 2013  
INVENTOR(S)      : James D. Kendall Page 1 of 1

It is certified that error appears in the above-identified patent and that said Letters Patent is hereby corrected as shown below:

In the Claims

Column 20, line 15 delete "method of claim 7" and replace with "apparatus of claim 8"

Signed and Sealed this
Sixteenth Day of July, 2013

Teresa Stanek Rea
*Acting Director of the United States Patent and Trademark Office*